United States Patent [19]

Hatton et al.

[11] Patent Number: 4,496,390
[45] Date of Patent: Jan. 29, 1985

[54] N-PHENYLPYRAZOLE DERIVATIVES

[75] Inventors: Leslie R. Hatton, Chelmsford; Edgar W. Parnell, Hornchurch; David A. Roberts, Bedford, all of England

[73] Assignee: May & Baker Limited, Essex, England

[21] Appl. No.: 398,337

[22] Filed: Jul. 15, 1982

Related U.S. Application Data

[63] Continuation-in-part of Ser. No. 237,661, Feb. 24, 1981, abandoned.

[30] Foreign Application Priority Data

| Feb. 26, 1980 | [GB] | United Kingdom | 806428 |
| Jul. 17, 1981 | [GB] | United Kingdom | 8122143 |
| Jul. 17, 1981 | [GB] | United Kingdom | 8122142 |
| Feb. 5, 1982 | [GB] | United Kingdom | 8203371 |
| Feb. 5, 1982 | [GB] | United Kingdom | 8203369 |

[51] Int. Cl.$^3$ ............................................. A01N 43/56
[52] U.S. Cl. ......................................... 71/92; 548/377
[58] Field of Search ............................................. 71/92

[56] References Cited

U.S. PATENT DOCUMENTS

| 3,646,059 | 2/1972 | Brantley | 71/92 |
| 3,869,274 | 3/1975 | Crovetti et al. | 71/92 |
| 3,883,550 | 5/1975 | Goddard | 71/92 |
| 4,260,775 | 4/1981 | Plath et al. | 71/92 |
| 4,298,749 | 11/1981 | Plath et al. | 71/92 |

FOREIGN PATENT DOCUMENTS

| 2180 | 10/1978 | European Pat. Off. | 71/92 |
| 39-20731 | 9/1964 | Japan | 71/92 |
| 39-23740 | 10/1964 | Japan | 71/92 |
| 29598 | 9/1965 | Japan | 71/92 |

OTHER PUBLICATIONS

Marsico et al., "Antiinflammatory 5-Amino- etc.;" (1973) CA84, No. 47987u, (1974).
Southwick et al., "Preparation of 4,6-, etc.;" (1975) CA84, No. 105,532n, (1976) (complete article attached).
Kreutzberger et al., "Antibacterial Agents, etc.;" (1979) CA92, No. 198346h, (1980) (complete article attached).
Towne et al., "Monoazopyrazole Dyes;" (1967) CA68, No. 14072r, (1968).
EPO No. 53678, "5-Amino-1-Phenyl-4-Cyano, etc.;" (1980) Derwent 50453 (1982).
EPO No. 53698, "5-Amino-1-Phenylpyrazole, etc.;" (1981) Derwent 50464 (1982).
DE 3,129,429, "5-Amino-1-Phenylpyrazole, etc.;" (1981) Derwent 15048 (1983).
J5-8135-810A, "Antitumour Phenyl Pyrazole, etc.;" (1982) Derwent 83-767941/33 (1983).
EGE et al., "Aminopyrazoles IV (1) Pyrazole-3, etc.;" (1982), J. Hetero. Chem. 19, pp. 1267–1273 (1982).
Kreutzberger et al., "Diuretics III 1-Carbocyclyl etc.;" (1981) CA95, No. 80881n, (1981).
DL 143-426, "5,6-Fused 4-Amino-3-Cyano, etc.;" (1980) CA95, No. 25039u, (1981).
J5 8208-275 A, "5-Amino Pyrazole, etc.;" (1983) Derwent 84-014938/02 (1983).

Primary Examiner—Glennon H. Hollrah
Attorney, Agent, or Firm—Stevens, Davis, Miller & Mosher

[57] ABSTRACT

N-Phenylpyrazole derivatives of the formula:

(wherein each of $R^5$ and $R^6$ represents a $C_1$–$C_4$ alkyl or alkoxy radical, a trifluoromethyl, trifluoromethoxy, nitro, cyano or primary amino radical, or a fluorine, chlorine or bromine atom, each of $R^7$, $R^8$ and $R^9$ represents a hydrogen atom, a $C_1$–$C_4$ alkyl or alkoxy radical, a trifluoromethyl, trifluoromethoxy, nitro, cyano or primary amino radical or a fluorine, chlorine or bromine atom, or $R^5$, $R^7$, $R^8$ and $R^9$ each represents a hydrogen atom and $R^6$ represents a trifluoromethoxy or trifluoromethyl radical, and $R^{10}$ represents a cyano radical or substituted carbamoyl radical —CONHR$^{11}$, wherein $R^{11}$ represents a methyl or ethyl radical) have been found to possess useful herbicidal properties. All such N-phenylpyrazole derivatives with the exception of 5-amino-4-cyano-1-(2,4-dichlorophenyl)pyrazole and 5-amino-4-cyano-1-(4-chloro-2-methylphenyl)pyrazole are new compounds. Herbicidal compositions containing such N-phenylpyrazole derivatives are described and also processes for the preparation of the new compounds.

30 Claims, No Drawings

N-PHENYLPYRAZOLE DERIVATIVES

This application is a continuation-in-part of our U.S. patent application No. 237,661, filed Feb. 24, 1981 now abandoned.

This invention relates to N-phenylpyrazole derivatives, compositions containing them and their use as herbicides.

In J. Heter. Chem., 12 (1975), 1199–1205, P. L. Southwick and B. Dhawan have described experiments for the preparation of 4,6-diaminopyrazolo[3,4-d]pyrimidines in the expectation that such pyrimidine derivatives would have useful pharmacological properties. They employed as starting materials 1-phenyl-5-amino-4-cyanopyrazoles of the general formula:

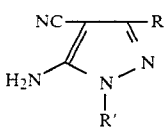

wherein R represents inter alia a hydrogen atom, and R' represents a hydrogen atom, a methyl group, a hydroxyethyl group or a phenyl group substituted by one or more chlorine atoms and/or methyl groups. Included amongst numerous pyrazole compounds prepared and disclosed by Southwick and Dhawan were 5-amino-4-cyano-1-(2,4-dichlorophenyl)pyrazole and 5-amino-4-cyano-1-(4-chloro-2-methylphenyl)pyrazole. This publication contains no suggestion that compounds of general formula I possess or would be expected to possess herbicidal activity.

Apparently these pyrazole compounds did not lead (according to the authors of the article) to useful therapeutic (viz. antimalarial) 4,6-diamino-pyrazolo[3,4-d]pyrimidines.

In Japanese patent application No. 29598/63 (applied for by Takeda Chemical Industries Ltd: Publication No. 19958/65) there are disclosed pyrazole derivatives of the general formula:

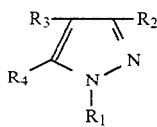

(wherein $R_1$ represents a hydrogen atom or an unsubstituted phenyl group, $R_2$ represents a hydrogen atom or a lower alkyl group, $R_3$ represents a hydrogen or halogen atom, or a nitro or cyano group, and $R_4$ represents a lower alkyl group, an amino group or a lower alkoxy group) which are useful as herbicides.

It has now unexpectedly been found after extensive research and experimentation that when the substituent $R_1$ on the pyrazole ring of compounds of general formula II is a phenyl radical carrying particular substituents, $R_2$ represents a hydrogen atom, $R_3$ represents a cyano or substituted carbamoyl radical, and $R_4$ represents an amino group, the compounds also have useful herbicidal activity and have unexpectedly advantageous herbicidal properties in relation to particular compounds disclosed in Japanese patent application No. 29598/63 (Publication No. 19958/65 -Derwent Basic No. G 3904), e.g. the closely related compound 1-phenyl-4-cyano-5-aminopyrazole.

The present invention accordingly provides, as herbicides, N-phenylpyrazole derivatives of the general formula:

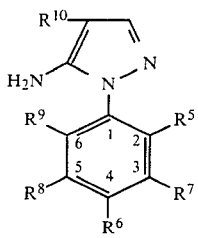

wherein each of the symbols $R^5$ and $R^6$, which may be the same or different, represents an alkyl or alkoxy radical containing from 1 to 4 carbon atoms, a trifluoromethyl, trifluoromethoxy, nitro, cyano or primary amino radical, or a fluorine, chlorine or bromine atom, each of the symbols $R^7$, $R^8$ and $R^9$, which may be the same or different, represents a hydrogen atom, an alkyl or alkoxy radical containing from 1 to 4 carbon atoms, a trifluoromethyl, trifluoromethoxy, nitro, cyano or primary amino radical or a fluorine, chlorine or bromine atom, or the symbols $R^5$, $R^7$, $R^8$ and $R^9$ each represents a hydrogen atom and the symbol $R^6$ represents a trifluoromethoxy or, preferably, a trifluoromethyl radical, and the symbol $R^{10}$ represents a cyano radical or substituted carbamoyl radical —$CONHR^{11}$ (wherein $R^{11}$ represents a methyl or ethyl radical) and, when at least one of symbols $R^5$, $R^6$, $R^7$, $R^8$ and $R^9$ represents a primary amino radical, agriculturally acceptable acid addition salts thereof. Preferably each of the symbols $R^5$ and $R^6$ represents an alkyl radical containing from 1 to 4 carbon atoms, a trifluoromethyl or nitro radical or a fluorine, chlorine or bromine atom; preferably $R^7$ represents a hydrogen atom, an alkyl or alkoxy radical containing from 1 to 4 carbon atoms, a cyano radical or a fluorine, chlorine or bromine atom; preferably each of the symbols $R^8$ and $R^9$ represents a hydrogen atom or a fluorine, chlorine or bromine atom, and preferably $R^{10}$ represents a cyano radical.

It is to be understood that in the present specification and accompanying claims the alkyl and alkoxy radicals within the definitions of the symbols $R^5$, $R^6$, $R^7$, $R^8$ and $R^9$ may be straight- or branched-chained. Preferably the alkyl radicals within the definitions of the symbols $R^5$, $R^6$, $R^7$, $R^8$ and $R^9$ are methyl; preferably the symbol $R^{11}$ represents methyl, and preferably the alkoxy radicals within the definitions of the symbols $R^5$, $R^6$, $R^7$, $R^8$ and $R^9$ are methoxy.

Particularly preferred compounds of general formula III as herbicides are those wherein each of $R^5$ and $R^6$ are as hereinbefore defined and more particularly represents an alkyl radical containing from 1 to 4 carbon atoms, a trifluoromethyl or nitro radical or a fluorine, chlorine or bromine atom, and more especially a methyl, trifluoromethyl or nitro radical or a fluorine, chlorine or bromine atom, $R^7$ is as hereinbefore defined and more particularly represents a hydrogen atom or, preferably, an alkyl or alkoxy radical containing from 1 to 4 carbon atoms, a cyano radical or a fluorine, chlorine or bromine atom, and more especially a methyl, methoxy or cyano radical, or a fluorine, chlorine or bromine atom, $R^8$ and $R^9$ represent hydrogen atoms, and $R^{10}$ is as hereinbefore defined and more particularly represents a cyano radical, and more especially compounds of general formula III hereinbefore defined as being particularly preferred wherein at least one of the symbols $R^5$, $R^6$ and $R^7$ represents a chlorine atom. 5-Amino-4-cyano-1-(2,3,4-trichlorophenyl)pyrazole is of outstanding importance as a herbicide.

By the term 'agriculturally acceptable acid addition salts' as used in the present specification is meant salts the anions of which are known and accepted in the art for the formation of salts of pesticidally active bases for agricultural or horticultural use. Suitable acid addition salts of the compounds of general formula III, wherein at least one of the symbols $R^5$, $R^6$, $R^7$, $R^8$ and $R^9$ represents a primary amino radical, include salts with inorganic acids, for example hydrochlorides, sulphates, phosphates and nitrates and salts with organic acids, for example acetic acid. It is to be understood that where reference is made in the present specification to the compounds of general formula III, such reference is intended to include also the agriculturally acceptable acid addition salts of compounds of general formula III, where appropriate.

The following compounds of general formula III are of particular interest as herbicides:

| Compound | |
|---|---|
| A | 5-amino-4-cyano-1-(2,3,4-trichlorophenyl)pyrazole |
| B | 5-amino-4-cyano-1-(2-nitro-4-trifluoromethylphenyl)pyrazole |
| C | 5-amino-4-cyano-1-(2,4-dichlorophenyl)pyrazole |
| D | 5-amino-1-(2-bromo-3,4-dichlorophenyl)-4-cyanopyrazole |
| E | 5-amino-4-cyano-1-(3,4-dichloro-2-methylphenyl)pyrazole |
| F | 5-amino-1-(3-bromo-2,4-dichlorophenyl)-4-cyanopyrazole |
| G | 5-amino-4-cyano-1-(2,4-dichloro-3-methylphenyl)pyrazole |
| H | 5-amino-4-cyano-1-(2,4-dichloro-3-methoxyphenyl)pyrazole |
| J | 5-amino-4-cyano-1-(3-cyano-2,4-dichlorophenyl)pyrazole |
| K | 5-amino-1-(4-bromo-2,3-dichlorophenyl)-4-cyanopyrazole |
| L | 5-amino-4-cyano-1-(2,3-dichloro-4-methylphenyl)pyrazole |
| M | 5-amino-4-cyano-1-(4-bromo-2-chloro-3-methylphenyl)pyrazole |
| N | 5-amino-4-cyano-1-(2-chloro-3,4-dimethylphenyl)pyrazole |
| P | 5-amino-4-cyano-1-(2-chloro-3-cyano-4-methylphenyl)pyrazole |
| Q | 5-amino-1-(3-chloro-2,4-dibromophenyl)-4-cyanopyrazole |
| R | 5-amino-1-(3-chloro-2,4-dimethylphenyl)-4-cyanopyrazole |
| S | 5-amino-1-(2-bromo-4-chloro-3-methylphenyl)-4-cyanopyrazole |
| T | 5-amino-1-(4-chloro-2,3-dimethylphenyl)-4-cyanopyrazole |
| U | 5-amino-1-(4-chloro-3-cyano-2-methylphenyl)-4-cyanopyrazole |
| V | 5-amino-4-cyano-1-(2,4,5-trichlorophenyl)pyrazole |
| W | 5-amino-4-cyano-1-(2,4,6-trichlorophenyl)pyrazole |
| X | 5-amino-4-cyano-1-(2,3,4,5-tetrachlorophenyl)pyrazole |
| Y | 5-amino-4-cyano-1-(2,3,4,6-tetrafluorophenyl)pyrazole |
| Z | 5-amino-4-cyano-1-pentachlorophenylpyrazole |
| AA | 5-amino-4-cyano-1-pentafluorophenylpyrazole |
| BB | 5-amino-4-cyano-1-(4-trifluoromethylphenyl)pyrazole |

-continued

| Compound | |
|---|---|
| CC | 5-amino-4-cyano-1-(3-chloro-2,4-difluorophenyl)pyrazole |
| DD | 5-amino-4-N—methylcarbonamido-1-(2,3,4-trichlorophenyl)pyrazole |
| EE | 5-amino-4-N—ethylcarbonamido-1-(2,3,4-trichlorophenyl)pyrazole |
| FF | 5-amino-4-cyano-1-(2,6-dichloro-4-ethylphenyl)pyrazole |
| GG | 5-amino-1-(2-chloro-4-ethylphenyl)-4-cyanopyrazole |
| HH | 5-amino-4-cyano-1-(4-methyl-2,3,5,6-tetrafluorophenyl)pyrazole |
| JJ | 5-amino-1-(2-chloro-4-methylphenyl)-4-cyanopyrazole |
| KK | 5-amino-4-cyano-1-(4-methyl-2,3,6-trichlorophenyl)pyrazole |
| LL | 5-amino-1-(4-n-butyl-2,3,5,6-tetrafluorophenyl)-4-cyanopyrazole |
| MM | 5-amino-1-(2-chloro-4-isopropylphenyl)-4-cyanopyrazole |
| NN | 5-amino-4-cyano-1-(2,3-dichloro-4-ethylphenyl)pyrazole |
| PP | 5-amino-4-cyano-1-(4-ethyl-2,3,5,6-tetrafluorophenyl)pyrazole |
| QQ | 5-amino-1-(2-chloro-4-n-propylphenyl)-4-cyanopyrazole |
| RR | 5-amino-4-cyano-1-(2,6-dibromo-4-trifluoromethylphenyl)pyrazole |
| SS | 5-amino-4-cyano-1-(3,5-difluoro-2,4,6-trichlorophenyl)pyrazole |
| TT | 5-amino-4-cyano-1-(2,4-dichloro-6-methylphenyl)pyrazole |
| UU | 5-amino-1-(4-bromo-2,3,5,6-tetrafluorophenyl)-4-cyanopyrazole |
| VV | 5-amino-1-(4-chloro-2,3,5,6-tetrafluorophenyl)-4-cyanopyrazole |
| WW | 5-amino-1-(2-bromo-4-trifluoromethylphenyl)-4-cyanopyrazole |
| XX | 5-amino-1-(4-sec-butyl-2,3,5,6-tetrafluorophenyl)-4-cyanopyrazole |
| YY | 5-amino-4-cyano-1-(2,3,4,6-tetrachlorophenyl)pyrazole |

The letters of the alphabet A to H, J to N and P to YY are assigned to the above compounds for identification and easy reference hereafter in the present specification.

Particularly preferred compounds according to the present invention are, referring to the identification by letters of the alphabet indicated above, Compound C, and more especially Compounds D to H, J to N and P to U and, in particular, Compound A.

Accordingly, a feature of the present invention is a method for controlling the growth of weeds (i.e. undesired vegetation) at a locus which comprises applying to the locus a herbicidally effective amount of at least one N-phenylpyrazole derivative of general formula III. For this purpose, the N-phenylpyrazole derivatives are normally used in the form of herbicidal compositions (i.e. in association with compatible diluents or carriers suitable for use in herbicidal compositions), for example as hereinafter described.

The compounds of general formula III show herbicidal activity against dicotyledonous (i.e. broad-leafed) and monocotyledonous (e.g. grass) weeds by pre- and-/or, post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula III may be used to control the growth of broad-leafed weeds, for example, *Aethusa cynapium*,

*Abutilon theophrasti, Amaranthus retroflexus, Amsinckia intermedia, Anagallis arvensis, Anthemis arvensis, Atriplex patula, Bidens pilosa, Brassica nigra, Capsella bursa-pastoris, Chenopodium album, Chrysanthemum segetum, Cirsium arvense, Datura stramonium, Desmodium tortuosum, Emex australis, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochloria vaginalis, Papaver rhoeas, Physalis longifolia, Plantago lanceolata,* Polygonum spp., (e.g. *Polygonum aviculare, Polygonum convolvulus* and *Polygonum persicaria*), *Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Xanthium strumarium,* and grass weeds, for example, *Alopecurus myosuroides, Apera spica-venti, Agrostis stolonifera, Avena fatua, Avena ludoviciana,* Brachiaria spp., *Bromus sterilis, Bromus techtorum,* Cenchrus spp., *Cynodon dactylon, Digitaria sanquinalis, Echinochloa crus-galli, Eleusine indica, Setaria viridis* and *Sorghum halepense* and sedges, for example *Cyperus esculentus, Cyperus iria* and *Cyperus rotundus,* and *Eleocharis acicularis.*

The amounts of compounds of general formula III applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without casusing substantial permanent damage to the crop. In general, taking these factors into account, application rates between 0.1 kg and 20 kg of active material per hectare give good results. However, it is to be understood that higher or lower application rates may be used, depending upon the particular problem of weed control encountered.

The compounds of general formula III may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates between 0.25 kg and 8.0 kg, and preferably between 0.5 kg and 2.0 kg, more especially of the preferred compounds of general formula III hereinbefore specified, of active material per hectare are particularly suitable. More particularly, the compounds of general formula III may be used to control selectively the growth of broad leafed weeds, for example to control the growth of those broad leafed species hereinbefore mentioned, by pre- or, more especially, post-emergence application in a non-directional fashion, e.g. by non-directional spraying, to an area used for growing cereal crops before or after emergence of both the crop and weeds.

For this purpose, i.e. the selective control of broad leafed weeds by pre- or post-emergence application to an area used for growing cereal crops, application rates between 0.25 and 8.0 kg, and preferably between 0.5 kg and 2.0 kg, more especially of the preferred compounds of general formula III hereinbefore specified, of active material per hectare are particularly suitable.

The compounds of general formula III may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or planatations at application rates between 0.25 kg and 10.0 kg, and preferably between 1.0 kg and 4.0 kg, more especially of the preferred compounds of general formula III hereinbefore specified, of active material per hectare.

The compounds of general formula III may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g. by directional or non-directional spraying) at application rates between 5.0 kg and 20.0 kg, and preferably between 10.0 and 20.0 kg, more especially of the preferred compounds of general formula III hereinbefore specified, of active material per hectare are particularly suitable for this purpose.

When used to control the growth of weeds by pre-emegence application, the compounds of general formula III may be incorporated into the soil in which the weeds are expected to emerge. It will be appreciated that when the compounds of general formula III are used to control the growth of weeds by post-emergence application, i.e. by application to the aerial or exposed portions of emerged weeds, the compounds of general formula III will also normally come into contact with the soil and may also then exercise a pre-emergence control on later-germinating weeds in the soil.

Where especially prolonged weed control is required, the application of the compounds of general formula III may be repeated if required.

According to a further feature of the present invention, there are provided compositions suitable for herbicidal use comprising one or more of the N-phenylpyrazole derivatives of general formula III in association with, and preferably homogeneously dispersed in, one or more compatible herbicidally-acceptable diluents or carriers (i.e. diluents or carriers of the type generally accepted in the art as being suitable for use in herbicidal compositions and which are compatible with compounds of general formula III). The term "homogeneously dispersed" is used to include compositions in which the compounds of general formula III are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula III.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octylphenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates.

Suitably, herbicidal compositions according to the present invention may comprise from 0.05% to 10% of surface-active agent but, if desired, herbicidal compositions according to the present invention may comprise higher proportions of surface-active agent, for example up to 15% in liquid emulsifiable suspension concentrates and up to 25% in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula III with solid diluents or by impregnating the solid diluents or carriers with solutions of the compounds of general formula III in volatile solvents, evaporating the solvents and, if necessary, grinding the products so as to obtain powders. Granular formulations may be prepared by absorbing the compounds of general formula III (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agent (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula III may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of one or more compounds of general formula III, from 2 to 10% w/v of surface-active agent, from 0.1 to 5% w/v of thickener and from 15 to 87.9% by volume of water; wettable powders which comprise from 10 to 90% w/w of one or more compounds of general formula III, from 2 to 10% w/w of surface-active agent and from 10 to 88% w/w of solid diluent or carrier; liquid water soluble concentrates which comprise from 10 to 30% w/v of one or more compounds of general formula III, from 5 to 25% w/v of surface-active agent and from 45 to 85% by volume of water-miscible solvent, e.g. dimethylformamide; liquid emulsifiable suspension concentrates which comprise from 10 to 70% w/v of one or more compounds of general formula III, from 5 to 15% w/v of surface-active agent, from 0.1 to 5% w/v of thickener and from 10 to 84.9% by volume of organic solvent, and granules which comprise from 2 to 10% w/w of one or more compounds of general formula III, from 0.5 to 2% w/w of surface-active agent and from 88 to 97.5% w/w of granular carrier.

Herbicidal compositions according to the present invention may also comprise the compounds of general formula III in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [α-chloro-2,6-diethyl-N-(methoxymethyl)acetanilide], asulam [methyl(4-aminobenzenesulphonyl)carbamate], alloxydim Na [sodium salt of 2-(1-allyloxyaminobutylidene)-5,5-dimethyl-4-methoxycarbonylcyclohexane-1,3-dione], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4- dichlorophenyl-2-aminopropionate], bromoxynil [3,5-dibromo-4-hydroxybenzonitrile], butachlor [N-(butoxymethyl)-α-chloro-2,6-diethylacetanilide], butylate [S-ethyl N,N-diisobutyl(thiocarbamate)], carbetamide [D-N-ethyl-2-(phenylcarbamoyloxy)propionamide], chlorfenprop-methyl[methyl 2-chloro-3-(4-chlorophenyl)-propionate], chlorpropham [isopropyl N-(3-chlorophenyl)carbamate], chlortoluron ]N'-(3-chloro-4-methylphenyl)-N,N-dimethylurea], cyanazine [2-chloro-4-(1-cyano-1-methylethylamino)-6-ethylamino-1,3,5-triazine], cycloate [N'-cyclohexyl-N-ethyl-S-ethyl(thiocarbamate)], 2,4-D [2,4-dichlorophenoxyacetic acid], dalapon [2,2-dichloropropionic acid], 2,4-DB [4-(2,4-dichlorophenoxy)butyric acid], desmedipham [3-(ethoxycarbonylamino)phenyl N-phenyl-carbamate], diallate [S-2,3-dichloroallyl-N,N-di-isopropyl(thiocarbamate)], dicamba [3,6-dichloro-2-methoxybenzoic acid], dichlorprop [($\pm$)-2-(2,4-dichlorophenoxy)propionic acid], difenzoquat [1,2-dimethyl-3,5-diphenyl-pyrazolium salts], dimefuron {4-[2-chloro-4-(3,3-dimethylureido)phenyl]-2-t-butyl-1,3,4-oxadiazolin-5-one}, dinitramine [$N^1$,$N^1$-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate, flampropisopropyl [sopropyl ($\pm$)-2-(N-benzoyl-3-chloro-4-fluoroanilino)propionate], flampropmethyl [methyl ($\pm$)-2-(N-benzoyl-3-chloro-4-fluoroanilino)propionate], fluometuron [N'-(3-trifluoromethylphenyl)-N,N-dimethylurea], ioxynil [4-hydroxy-3,5-di-iodobenzonitrile], isoproturon [N'-(4-isopropylphenyl)-N,N-dimethylurea], linuron [N-(3,4-dichlorophenyl)-N-methoxy-N-methylurea], MCPA [4-chloro-2-methylphenoxyacetic acid], MCPB [4-(4-chloro-2-methylphenoxy)butyric acid], mecoprop· [-($\pm$)-2-(4-chloro-2-methylphenoxy)propionic acid], metamitron [4-amino-3-methyl-6-phenyl-1,2,4-triazin-5(4H)-one], methabenzthiazuron [N-(benzothiazol-2-yl)-N,N'-dimethylurea], metribuzin [4-amino-6-t-butyl-3-(methylthio)-1,2,4-triazin-5(4H)-one], molinate [S-ethyl N,N-hexamethylene(thiocarbamate)], oxadiazon [3-(2,4-dichloro-5-isopropoxyphenyl)-5-t-butyl-1,3,4-oxadiazolin-2-one], paraquat [1'-1-dimethyl-4,4'-bipyridylium salts], pebulate [S-propyl N-butyl-N-ethyl(thiocarbamate)], phenmedipham [-3-(methoxycarbonylamino)phenyl N-(3-methylphenyl)carbamate], prometryne [4,6-bisisopropylamino-2-methylthio-1,3,5-triazine], propachlor [α-chloro-N-isopropylacetanilide], propanil [N-(3,4-dichlorophenyl)propionanide], propham [isopropyl N-phenylcarbamate], pyrazone [5-amino-4-chloro-2-phenylpyridazin-3(2H)-one], simazine [2-chloro-4,6-bisethylamino-1,3,5-triazine], TCA (trichloroacetic acid), thiobencarb [S-(4-chlorobenzyl)-N,N-diethylthiolcarbamate], tri-allate[S-2,3,3-trichloroallyl N,N-di-isopropyl(thiocarbamate)] and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butylcarbamoyl-benzimidazol-2-yl)carbamate, 1,2-bis(3-methoxycarbonyl-2-thioureido)benzene, isopropyl 1-carbamoyl-3-(3,5-dichlorophenyl)hydantoin and 1-(4-chloro-phenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

When the diluent or carrier for the N-phenylpyrazole derivative of general formula III is water or a common organic solvent (e.g. toluene or xylene) and the active ingredient of the herbicidal composition is either of the previously known compounds 5-amino-4-cyano-1-(2,4-dichlorophenyl)pyrazole and 5-amino-4-cyano-1-(4-chloro-2-methylphenyl)pyrazole, another material should also be present, for example a surface-active agent, another pesticide, or a fertilizer, in order that the composition is other than an association of either of the two aforesaid pyrazole derivatives solely with water or a common organic solvent.

According to a further feature of the present invention there is provided an article of manufacture comprising at least one of the N-phenylpyrazole derivatives of general formula III or, as is preferred, a herbicidal composition as hereinbefore described, and preferably a herbicidal concentrate which must be diluted before use, comprising at least one of the N-phenylpyrazole derivative of general formula III within a container for the aforesaid derivative or derivatives of general formula III, or a said herbicidal composition, and instructions physically associated with the aforesaid container setting out the manner in which the aforesaid derivative or derivatives of general formula III or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally-lacquered, and plastics materials, bottles of glass and plastics materials and, when the contents of the container is a solid, for example granular, herbicidal compositions, boxes, for example of cardboard, plastics materials and metal, or sacks. The containers will normally be of sufficient capacity to contain amounts of the N-phenylpyrazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.1 kg and 20 kg of active material per hectare in the manner and for the purposes hereinbefore described.

The following Examples illustrate herbicidal compositions according to the present invention.

EXAMPLE 1

5-Amino-4-cyano-1-pentafluorophenylpyrazole was formulated as a water soluble concentrate containing

| | |
|---|---|
| 5-amino-4-cyano-1-pentafluorophenyl-pyrazole | 10% w/v (weight/volume) |
| Ethylan KEO (nonylphenyl/ethylene oxide condensate containing 9–10 moles of ethylene oxide per mol of phenol) | 10% w/v |
| Dimethylformamide | to 100% by volume, | by dissolving the Ethylan KEO in a portion of dimethylformamide and then adding the active ingredient with heating and stirring until dissolved. The resulting solution was then made up to 100% by volume by adding the rest of the dimethylformamide.

20 Liters of the above formulation may be dissolved in 200 liters of water and sprayed post-emergence onto 1 hectare of oilseed rape to control *Amaranthus retroflexus, Setaria viridis, Polygonum lapathifolium, Abutilon theophrasti* and *Solanum nigrum.*

The 5-amino-4-cyano-1-pentafluorophenylpyrazole may, if desired, be replaced in the above water soluble concentrate by any other compound of general formula III.

EXAMPLE 2

A wettable powder was formed from:

| | |
|---|---|
| 5-amino-4-cyano-1-(2,3,4-trichloro-phenyl)pyrazole | 50% w/w (weight/weight) |
| Ethylan BCP (a nonylphenol/ethylene oxide condensate containing 9 moles of ethylene oxide per mol of phenol) | 5% w/w |
| Aerosil (silicon dioxide of microfine particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder which may be diluted with water and applied at an application rate of 4 kg of wettable powder in 300 liters of spray fluid per hectare to control the growth of *Galium aparine, Veronica persica, Viola arvensis* and *Galeopsis tetrahit* by post-emergence application in an emerged crop of winter wheat.

Similar wettable powders may be prepared as described above by replacing the 5-amino-4-cyano-1-(2,3,4-trichlorophenyl)pyrazole by other compounds of general formula III.

EXAMPLE 3

An aqueous suspension concentrate was formed from:

| | |
|---|---|
| 5-amino-4-cyano-1-(2,3,4-trichloro-phenyl)pyrazole | 50% w/v |
| Ethylan BCP | 1.0% w/v |
| Sopropon T36 (sodium salt of polycarboxylic acid) | 0.2% w/v |
| Ethylene glycol | 5% w/v |
| Rhodigel 23 (polysaccharide xanthan gum thickener) | 0.15% w/v |
| distilled water | to 100% by volume | by intimately mixing the ingredients and grinding in a ball-mill for 24 hours. The concentrate thus obtained may be dispersed in water and applied at a application rate of 4 kg of aqueous suspension concentrate in 300 liters of spray fluid per hectare to control the growth of *Galium aparine, Veronica persica, Viola arvensis* and *Galeopsis tetrahit* by post-emergence application in an emerged crop of winter barley.

Similar aqueous suspension concentrates may be prepared as described above by replacing the 5-amino-4-cyano-1-(2,3,4-trichlorophenyl)pyrazole by other compounds of general formula III.

EXAMPLE 4

An emulsifiable suspension concentrate was formed from:

| | |
|---|---|
| 5-amino-4-cyano-1-(2,3,4-trichloro-phenyl)pyrazole | 50% w/v |
| Ethylan TU (a nonyl phenol/ethylene oxide condensate containing 10 moles of ethylene oxide per mol of phenol) | 10% w/v |
| Bentone 38 (an organic derivative of special magnesium montmorillonite thickener) | 0.5% w/v |
| Aromasol H (an aromatic solvent consisting predominantly of isomeric trimethylbenzenes) | to 100% by volume | by intimately mixing the ingredients and grinding in a ball-mill for 24 hours. The emulsifiable suspension concentrate thus obtained may be diluted with water and applied at an application rate of 3 kg of emulsifiable suspension concentrate in 100 liters of spray fluid per hectare to control the growth of *Setaria viridis, Polygonum convolvulus,* and *Chenopodium album* by post-emergence application in an emerged crop of spring-sown wheat.

Similar emulsifiable suspension concentrates may be prepared as described above by replacing the 5-amino-4-cyano-1-(2,3,4-trichlorophenyl)pyrazole by other compounds of general formula III.

EXAMPLE 5

Granules were formed from:

| | |
|---|---|
| 5-amino-4-cyano-1-(2,3,4-trichloro-phenyl)pyrazole | 5% w/w |
| Ethylan BCP | 1% w/w |
| Oleic acid | 1% w/w |
| Aromasol H | 12% w/w |
| 30/60 Attapulgite granules (sorptive silica clay) | 81% w/w | by mixing the phenylpyrazole, Ethylan BCP, oleic acid and Aromasol H and spraying the mixture onto the Attapulgite granules. The granules thus obtained may applied at an application rate of 50 kg of granules per hectare to control the growth of *Echinochloa crusgalli, Eleocharis acicularis* and *Monochoria vaginalis* by pre-emergence application or application to seedling weeds in a crop of transplanted paddy rice.

Similar granules may be prepared as described above by replacing the 5-amino-4-cyano-1-(2,3,4-trichlorophenyl)pyrazole by other compounds of general formula III.

EXAMPLE 6

A water soluble concentrate was formed from:

| | |
|---|---|
| 5-amino-4-cyano-1-(2,3,4-trichloro-phenyl)pyrazole | 10% w/v |
| Ethylan KEO | 10% w/v |
| Dimethylformamide | to 100% by volume | by dissolving the Ethylan KEO in a portion of dimethylformamide and then adding the pyrazole derivative with heating and stirring until dissolved. The resulting solution was then made up to 100% by volume with dimethylformamide by adding the rest of the dimethylformamide. The water soluble concentrate thus obtained may be diluted with water and applied at an application rate of 10 liters of water soluble concentrate in 200 to 2000 liters of spray fluid per hectare to control the growth of *Galium aparine, Veronica persica, Viola arvensis* and *Galeopsis tetrahit* by post-emergence application in an emerged crop of winter wheat at the tillering growth stage.

EXAMPLE 7

A wettable powder was formed from:

| | |
|---|---|
| 5-amino-4-cyano-1-(2,3,4-trichlorophenyl)-pyrazole | 90% w/w |
| Arylan S (sodium dodecyl benzene sulphonate) | 2% w/w |
| Darvan No. 2 (sodium lignosulphate) | 5% w/w |
| Celite PF | 3% w/w | by mixing the ingredients and grinding the mixture in a hammer-mill to give a wettable powder which may be diluted with water and applied at an application rate of 2 kg of wettable powder in 300 liters of spray fluid per hectare to control the growth of *Galium aparine, Veronica persica, Viola arvensis* and *Galeopsis tetrahit* by post-emergence application in an emerged crop of winter wheat.

Similar wettable powders may be prepared as described above by replacing the 5-amino-4-cyano-1-(2,3,4-trichlorophenyl)pyrazole by other compounds of general formula III.

EXAMPLE 8

A wettable powder containing 50% w/w of 5-amino-4-cyano-1-(2,3,4-trichlorophenyl)pyrazole, prepared as hereinbefore described in Example 2, may be diluted with water and applied at an application rate of 0.5 kg of wettable powder in 300 liters of spray fluid per hectare to control the growth of *Abutilon theophrasti* and *Polygonum lapathifolium* by post-emergence application at the early seedling growth stage of these weeds in a crop of spring wheat.

EXAMPLE 9

A wettable powder containing 50% w/w of 5-amino-4-cyano-1-(2,3,4-trichlorophenyl)pyrazole, prepared as described in Example 2, may be diluted with water and applied at an application rate of 40 kg of wettable powder in 600 liters of spray fluid per hectare to produce a total herbicidal effect on vegetation at a locus which is not a crop-growing area.

In experiments on herbicidal activity carried out on representative compounds of general formula III, the closely related compound 1-phenyl-4-cyano-5-aminopyrazole specifically disclosed in Japanese patent application No. 29598/1963 (test compound CC1) and the closely related compound 5-amino-4-cyano-1-(2,3,4-trichlorophenyl)-3-methylpyrazole (test compound CC2), the following results have been obtained:

EXPERIMENT 1

Test Method (1) Weed Control Test (a) General

The test compounds A to H, J to N and P to JJ, CC1 and CC2 (as hereinbefore identified) were dissolved in acetone. Application was from a standard laboratory herbicide sprayer using a flat fan jet travelling at 1.6 m.p.h. (2.6 km/hour) and delivering the equivalent of 530 liters of spray fluid per hectare, the spray pressure being 2.81 kg/cm$^2$ (40 pounds/inch$^2$). The solutions of test compounds A to H, J, K, M, N and Q to EE, CC1 and CC2 were prepared by dissolving 0.513 g of test compound in acetone and making up with more acetone to 34 ml (1.5% w/v), equivalent to an application rate of 8 kg of test compound per hectare. Solutions equivalent to 4, 2, 1, 0.5, 0.25 and 0.125 kilogrammes per hectare (kg/ha) were prepared from these solutions by serial dilution with acetone, except for test compounds C, W, AA, BB, DD, EE and CC1 for which solutions equivalent to 8, 4, 2, 1 and 0.5 kg/ha were prepared. The solutions of test compounds L and P were similarly prepared but using 0.128 g of test compound to give solutions equivalent to application rates of 2, 1, 0.5, 0.25 and 0.125 kg/ha. The solutions of test compound FF were similarly prepared but using 0.256 g of test compound to give solutions equivalent to application rates of 4, 2, 1, 0.5 0.25 and 0.125 kg/ha. The solutions of test compounds GG and JJ were similarly prepared but using 0.128 g of test compound to give solutions equivalent to application rates of 2, 1, 0.5, 0.25, 0.125, 0.063 and 0.0312 kg/ha. The solution of test compound HH was similarly prepared but using 0.064 g of test compound to give solutions equivalent to 1, 0.5, 0.25, 0.125, 0.063, 0.312, 0.0156, 0.0078 and 0.0039 kg/ha. The solution of test compound YY was similarly prepared but using 0.256 g of test compound to give solutions equivalent to 4, 2, 1, 0.5, 0.25, 0.125, 0.063, 0.031, and 0.0156 kg/ha.

(b) Weed Control Pre-emergence application

Weed seeds were sown on the surface of John Innes No. 1 potting compost (7 parts by volume of sterilized loam, 3 parts by volume of peat and 2 parts by volume of fine grit) in 9 cm diameter bitumenised paper pots. The quantities of seeds per pot were as follows:

| Weed species | Approximate number seeds/pot |
|---|---|
| (i) Broad leafed weeds | |
| *Sinapis arvensis* | 30–40 |
| *Polygonum lapathifolium* | 30–40 |
| *Stellaria media* | 30–40 |
| (ii) Grass weeds | |
| *Avena fatua* | 15–20 |
| *Alopecurus myosuroides* | 30–40 |
| *Echinochloa crus-galli* | 20–30 |

The test compounds were applied to the uncovered seeds as described in (1) (a) above at dose rates of 0.125 to 8 kg/ha, except for test compounds L and P, which were applied at dose rates of 0.125 to 2 kg/ha, and for test compounds C, W, AA, BB, DD, EE and CC1 which were applied at dose rates of 0.5 to 8 kg/ha, and the seeds were covered with 25 ml of sharp sand after spraying. A single pot of each weed species was allocated to each treatment, with unsprayed controls and controls sprayed with acetone alone. After treatment, the pots were kept in the greenhouse and were watered overhead. Visual assessment of weed control activity was made 19 to 28 days after spraying. The results were expressed as the minimum effective dose (MED) in kg/ha which gave 90% reduction in growth or kill of the weeds in comparison with plants in the control pots. The results obtained are presented below in Table I.

(c) Weed Control: Post-emergence application

Weed species were grown and then transplanted at the seedling stage into John Innes No. 1 potting compost in 9 cm diameter bituminised paper pots, except for *Avena fatua*, which was sown directly in the test pot and not transplanted. The plants were then grown in the greenhouse until ready for spraying with the test compounds. The number of plants per pot and the growth stage of the plant at spraying were as follows:

| Weed species | Number of plants/pot | Growth stages at spraying |
|---|---|---|
| (i) Broad leafed weeds | | |
| *Polygonum lapathifolium* | 5 | 1–1½ pairs of leaves |
| *Stellaria media* | 5 | 4–6 leaves |
| *Abutilon theophrasti* | 3 | 2 pairs of leaves |
| (ii) Grass weeds and Sedges | | |
| *Avena fatua* | 10 | 1 leaf |
| *Alopecurus myosuroides* | 5 | 1½ leaves |
| *Echinochloa crus-galli* | 5 | 1–2 leaves |
| *Cyperus Rotundus* | 3 | 2–3 leaves |

The test compounds were applied to the plants as described in (1) (a) above at dose rates of from 0.125 to 8 kg/ha except for test compounds L and P, which were applied at dose rates of 0.125 to 2 kg/ha and for test compounds C, W, AA, BB, DD, EE and CC1 which were applied at dose rates of 0.5 to 8 kg/ha. A single pot of each weed species was allocated to each treatment, with unsprayed controls and controls sprayed with acetone alone. After spraying, the pots were watered overhead, commencing 24 hours after spraying. Assessment of the control of the growth of the weeds was made 19–28 days after spraying by recording the number of plants which had been killed and the reduction in growth. The results were expressed as the minimum effective dose (MED) in kg/ha which gave 90% reduction in growth or kill of the weeds in comparison with the plants in the control pots. The results obtained are presented below in Table II.

KEY TO WEED SPECIES (a) Grass Weeds and Sedges

Am = *Alopecurus myosuroides*
Af = *Avena fatua*
Ec = *Echinochloa crus-galli*
Cr = *Cyperus rotundus*

(b) Broad-Leaf Weeds

Sm = *Stellaria media*
Pl = *Polygonum lapathifolium*
Sa = *Sinapis arvensis*
At = *Abutilon theophrasti*

TABLE I

| Test Compound | PRE-EMERGENCE MED (kg/ha) | | | | | |
|---|---|---|---|---|---|---|
| | Pl | Sa | Sm | Am | Af | Ec |
| A | 0.25 | 0.125 | 0.5–1 | 0.5 | 0.5–1 | 0.125–0.25 |
| B | 0.5–1 | 0.5 | >8 | 2 | 2–4 | 1–2 |
| C | 0.5–1 | 0.5–1 | 8 | 4 | 4 | 1 |
| D | 0.5–1 | 0.25–0.5 | 4–8 | 2 | 4 | 1 |
| E | 1 | 1–2 | 2–4 | 2–4 | 2–4 | 0.5–1 |
| F | 0.5–1 | 0.5–1 | 2 | 2–4 | 1–2 | 0.5–1 |
| G | 0.25–0.5 | 0.25–0.5 | 0.5 | 1–2 | 1–2 | 0.25–0.5 |
| H | 0.5–1 | 2 | 1 | 2 | 1–2 | 2 |
| J | 0.5 | 0.5–1 | 4–8 | 2 | 1–2 | 1 |
| K | 1 | 0.5 | 1–2 | 2–4 | 2–4 | 1 |
| L | 0.5 | 1 | >>2 | >2 | >2 | 1–2 |
| M | 1 | 0.5–1 | >8 | 4 | 4 | 0.5–1 |
| N | 0.125–0.25 | 0.25 | 8 | 4 | 2–4 | 0.25–0.5 |
| P | 1 | >>2 | NR | NR | NR | 2 |
| Q | 4 | 4 | 4 | 4–8 | 4–8 | 4–8 |
| R | 1–2 | 4–8 | >8 | 2–4 | 2–4 | 1–2 |
| S | 1–2 | 0.5–1 | 2–4 | 4 | 4 | 4 |
| T | 0.5–1 | 2–4 | 4–8 | 0.5–1 | 2–4 | 2–4 |
| U | 2 | 4–8 | 4–8 | 2–4 | >8 | 2 |
| V | 1 | 2 | 8 | 8 | 4–8 | 1 |
| W | 0.5–1 | <0.5 | 2 | 2–4 | 0.5–1 | 0.5–1 |
| X | 2 | 1–2 | 0.5 | 2–4 | 2–4 | 2 |
| Y | 0.5 | 1.0 | 4–8 | 2–4 | 2 | 0.5–1 |
| Z | 2–4 | 1–2 | >>8 | 2–4 | 4–8 | 1 |
| AA | 1–2 | 1.0 | 8 | 2–4 | 1–2 | 1 |
| BB | 1–2 | 4 | 4–8 | 2–4 | 4 | 1–2 |
| CC | 1 | 4 | >>8 | 4 | 4 | 1 |
| DD | 4 | 1 | 8 | >>8 | NR | >8 |
| EE | NR | 2–4 | NR | NR | NR | >>8 |
| FF | 0.5 | 2–4 | >>4 | >4 | 4 | 1 |
| GG | 0.5–1 | >2 | >2 | >>2 | >>2 | 2 |
| HH | 0.125 | 0.125–0.25 | >>1 | 1 | 0.5–1 | 0.25 |
| JJ | 1–2 | NR | NR | >>2 | NR | >>2 |
| YY | 1–2 | 0.125–0.25 | 2–4 | 2 | 2 | 0.5–1 |
| CC1 | 8 | >>8 | 8 | NR | NR | >>8 |
| CC2 | NR | NR | NR | NR | NR | NR |

TABLE II

| Test Compound | POST-EMERGENCE MED (kg/ha) | | | | | | |
|---|---|---|---|---|---|---|---|
| | At | Pl | Sm | Am | Af | Ec | Cr |
| A | 0.125 | 0.125 | 1–2 | 4–8 | 4–8 | 2–4 | |
| B | 0.125 | 0.5 | >8 | >>8 | >8 | 8 | |
| C | <0.5 | <0.5 | >>8 | >8 | >8 | 4 | |
| D | 0.125–0.25 | 0.125–0.25 | 2–4 | >8 | >>8 | >8 | |
| E | <0.125 | <0.125 | 2 | >>8 | >8 | 8 | |
| F | 0.125–0.25 | 0.25–0.5 | 0.5–1 | NR | >>8 | >8 | |
| G | <0.125 | 0.25–0.5 | 4–8 | >>8 | >8 | 4 | |
| H | 0.25 | 0.125–0.25 | 0.25 | >8 | 8 | 1–2 | |
| J | <0.125 | <0.125 | NR | >8 | >8 | 1–2 | |
| K | 0.25– | 0.125– | 2 | NR | >8 | >8 | |

TABLE II-continued

| Test Compound | POST-EMERGENCE MED (kg/ha) | | | | | | |
|---|---|---|---|---|---|---|---|
| | At | Pl | Sm | Am | Af | Ec | Cr |
| L | 0.5<br><0.125 | 0.25<br>0.25–0.5 | >2 | >>2 | >>2 | 2 | |
| M | 0.125–0.25 | 0.25–0.5 | >8 | NR | >>8 | >8 | |
| N | 0.125–0.25 | 0.25–0.5 | NR | >>8 | >>8 | 8 | |
| P | 0.125–0.5–1 | >>2 | >>2 | >>2 | NR | | |
| | 0.25 | | | | | | |
| Q | 0.125–0.25 | 0.25 | 4–8 | >>8 | >>8 | >>8 | |
| R | 0.125–0.25 | 0.25–0.5 | NR | >>8 | >>8 | >8 | |
| S | 0.125–0.25 | 0.25–0.5 | 1–2 | NR | >>8 | >8 | |
| T | 0.5–1 | 0.5–1 | NR | >>8 | >8 | >8 | |
| U | 1–2 | 0.5–1 | >>8 | >>8 | >>8 | >8 | |
| V | 0.25–0.5 | 0.5 | >>8 | >>8 | >>8 | >8 | |
| W | <0.5 | <0.5 | >>8 | >8 | 8 | 2–4 | |
| X | 0.5–1 | 0.5–1 | 2 | NR | NR | >8 | |
| Y | 0.125–0.25 | 0.25–0.5 | >>8 | 8 | 4–8 | 2 | |
| Z | 0.5–1 | 1–2 | NR | >8 | NR | >8 | |
| AA | <0.5 | <0.5 | NR | 8 | 4 | 2–4 | |
| BB | 1 | 0.5–1 | NR | >>8 | >>8 | 4–8 | |
| CC | 2–4 | 2 | NR | >>8 | >8 | 4 | |
| DD | 1–2 | >8 | NR | NR | NR | >>8 | |
| EE | 4–8 | 8 | NR | NR | NR | >>8 | |
| FF | 0.25–0.5 | 0.25–0.5 | NR | >>8 | NR | >>8 | NR |
| GG | 0.125 | 0.25 | NR | NR | NR | >>2 | NR |
| HH | 0.0078–0.0156 | 0.0156 | >>1 | 1.0 | >>1 | >>1 | >>1 |
| JJ | 0.5 | 1–2 | NR | >>2 | NR | >>2 | NR |
| YY | <0.0156 | 0.125 | 1–2 | >>4 | >4 | >4 | NR |
| CC1 | >>8 | >>8 | NR | >>8 | >>8 | NR | |
| CC2 | NR | NR | NR | NR | >>8 | NR | |

EXPERIMENT 2

Test Method

Test Procedure

The solutions of the test compounds were prepared by dissolving the test compounds in acetone. Application was from a standard laboratory herbicide sprayer using a flat fan jet travelling at 1.6 m.p.h. (2.6 km/hour) and delivering the equivalent of 530 liters of spray fluid per hectare, the spray pressure being 2.81 kg/cm$^2$ (40 pounds/inch$^2$). The solutions of the test compounds were prepared by dissolving 0.0755 g of test compound in acetone (20 ml), equivalent to an application rate of 2000 g of test compound per hectare. Solutions equivalent to application rates of 500, 125, 31, 8 and 2 g/ha test compound were then prepared by four-fold serial dilution with acetone.

(b) Weed Control: Pre-emergence application

Weed seeds were sown on the surface of John Innes No. 1 potting compost (7 parts by volume of sterilized loam, 3 parts by volume of peat and 2 parts by volume of fine grit) in 7 cm-square plastic pots. The quantities of seeds per pot were as follows:

| Weed species | Approximate number of seeds/pot |
|---|---|
| (i) Broad leafed weeds | |
| Chenopodium album | 50 |
| Sinapis arvensis | 30–40 |
| Abutilon theophrasti | 15 |
| Ipomea purpurea | 8 |
| (ii) Grass weeds and sedges | |
| Avena fatua | 15–20 |
| Echinochloa crus-galli | 30 |
| Cyperus rotundus | 3 nuts |

The test compounds were applied as described above and the seeds were covered with 25 ml of sharp sand after spraying. A single pot of each weed species was allocated to each treatment, with unsprayed controls and controls sprayed with acetone alone. After treatment, the pots were kept in the greenhouse and watered overhead. Visual assessment of % age weed destruction was made 21 days after spraying, in comparison with unsprayed controls. The % age weed destruction figures were then plotted against application rates on logarithmic-arithmetic paper to calculate the effective dose (ED$_{90}$) which produced 90% destruction of weeds. The results obtained are presented below in Table III.

(c) Weed Control: Post-emergence application

Weed species were grown and then transplanted at the seedling stage into John Innes No. 1 potting compost in 7 cm-square plastic pots, except for Avena fatua, which was sown directly in the test pot and not transplanted. The plants were then grown in the greenhouse until ready for spraying with the test compounds. The number of plants per pot and the growth stage of the plant at spraying were as follows:

| Weed species | Number of plants/pot | Growth stage at spraying |
|---|---|---|
| (i) Broad leafed weeds | | |
| Chenopodium album | 4 | 4 leaves |
| Sinapis arvensis | 4 | 2 leaves |
| Abutilon theophrasti | 3 | 1-2 leaves |
| Ipomea purpurea | 3 | 2 leaves |
| (iii) Grass weeds and sedges | | |
| Avena fatua | 10 | 1-2 leaves |
| Echinochloa crus-galli | 4 | 1-2 leaves |
| Cyperus rotundus | 3 | 2-3 leaves |

The test compounds were applied as described above. A single pot of each weed species was allocated to each treatment, with unsprayed controls and controls sprayed with acetone alone. After spraying, the pots were kept in the greenhouse and water overhead, commencing 24 hours after spraying. Visual assessment of % age weed destruction in comparison with unsprayed controls was made 14 days after spraying. The $ED_{90}$ values were then calculated as described above. The results obtained are presented below in Table IV.

KEY TO WEED SPECIES (a) Grass Needs And Sedges

Af = *Avena fatua*
Ec = *Echinochloa crus-galli*
Am = *Alopecurus myosuroides*
Cr = *Cyperus rotundus*

(b) Broad Leaf Weeds

Sm = *Stellaria media*
Pl = *Polygonum lapathifolium*
Sa = *Sinapis arvensis*
At = *Abutilon theophrasti*
Ca = *Chenopodium album*
Ip = *Ipomea purpurea*

TABLE III

| | PRE-EMERGENCE ED90 (g/ha) | | | | | | | |
|---|---|---|---|---|---|---|---|---|
| Test Compound | Ca | Sa | At | Ip | Af | Ec | Cr | Application Rates applied (g/ha) |
| KK | 25 | 58 | 290 | 1200 | >>2000 | 500 | >>2000 | 8-2000 |
| LL | — | 230 | 200 | >>2000 | >>2000 | >>2000 | NR | 8-2000 |
| MM | — | 440 | 24 | 1100 | >>2000 | 2000 | >>2000 | 8-2000 |
| NN | — | 500 | 84 | 2000 | 1800 | 500 | >>2000 | 8-2000 |
| PP | — | 30 | 28 | 230 | 900 | 275 | 460 | 8-2000 |
| QQ | — | 1000 | 125 | >2000 | >>2000 | >2000 | NR | 8-2000 |
| RR | — | 32 | 56 | 420 | 2000 | 500 | >2000 | 8-2000 |
| SS | 490 | 500 | 1900 | 220 | >>2000 | 1700 | 2000 | 8-2000 |
| TT | — | 430 | 480 | 1700 | NR | 2000 | — | 8-2000 |
| UU | 500 | 80 | 30 | 110 | 500 | 260 | 2000 | 8-2000 |
| VV | 32 | 30 | 8 | 60 | 450 | 430 | 800 | 8-2000 |
| WW | 500 | 110 | 60 | 200 | 1000 | 640 | 2000 | 8-2000 |
| XX | <8 | 1700 | 42 | >>2000 | NR | 280 | >>2000 | 8-2000 |

TABLE IV

| | POST-EMERGENCE ED90 (g/ha) | | | | | | | |
|---|---|---|---|---|---|---|---|---|
| Test Compound | Ca | Sa | At | Ip | Af | Ec | Cr | Application Rates applied (g/ha) |
| KK | 250 | 500 | 200 | 580 | >>2000 | >>2000 | NR | 8-2000 |
| LL | 125 | 1000 | <8 | >2000 | >>2000 | >>2000 | NR | 8-2000 |
| MM | 500 | 2000 | 400 | >2000 | >>2000 | >>2000 | NR | 8-2000 |
| NN | 84 | 720 | 240 | >2000 | >>2000 | >>2000 | NR | 8-2000 |
| PP | 31 | 125 | <8 | 30 | 2000 | 440 | 2000 | 8-2000 |
| QQ | 200 | >2000 | 56 | >2000 | >>2000 | >>2000 | NR | 8-2000 |
| RR | 32 | 110 | 94 | 56 | >>2000 | 2000 | NR | 8-2000 |
| SS | 220 | 1700 | 500 | 72 | NR | >>2000 | >>2000 | 8-2000 |
| TT | 950 | 1700 | 30 | 430 | NR | >>2000 | NR | 8-2000 |
| UU | 32 | 125 | 32 | 25 | >>2000 | 1700 | >>2000 | 8-2000 |
| VV | 56 | 190 | 32 | <8 | >2000 | 940 | >2000 | 8-2000 |
| WW | 500 | 300 | 62 | 62 | >>2000 | >>2000 | NR | 8-2000 |
| XX | >2000 | 1000 | 125 | 700 | >>2000 | NR | NR | 8-2000 |

The following symbols which appear in the above Tables have the following meanings:
>> means = much greater than
> means = greater than
< means = less than
NR means = no reduction at any dose rate applied
— means = not tested The above experimental results clearly demonstrate the valuable herbicidal properties of the compounds of general formula III and the surprising and unexpected superiority in herbicidal activity possessed by the compounds of general formula III in comparison with the closely related compound 1-phenyl-4-cyano-5-aminopyrazole disclosed in Japanese patent application No. 29598/63 and a closely related compound 5-amino-4-cyano-1-(2,3,4-trichlorophenyl)-3-methylpyrazole in which substitution of the 3-position of the pyrazole ring by alkyl (methyl) as taught in Japanese patent application No. 29598/63 is combined with substitution in the 1-position of the pyrazole ring by a substituted phenyl group (2,3,4-trichlorophenyl) found to confer high herbicidal activity in the compounds of general formula III.

According to a feature of the present invention, the new N-phenylpyrazole derivatives of general formula III, wherein $R^5$, $R^6$, $R^7$, $R^8$ and $R^9$ are as hereinbefore defined and $R^{10}$ represents a cyano radical, are prepared by the process which comprises the cyclisation of a compound of the general formula:

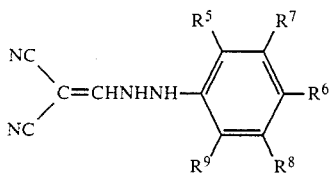  IV wherein the various symbols are as hereinbefore defined. Cyclisation may be effected in the presence of an inert organic solvent, for example an alkanol containing from 1 to 4 carbon atoms e.g. ethanol), acetic acid or ethoxyethanol, at a temperature of from ambient temperature up to the reflux temperature of the reaction mixture.

Compounds of general formula IV may be prepared by the reaction of a compound of the general formula:

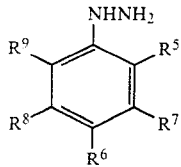  V (wherein the various symbols are as hereinbefore defined) or an acid addition salt thereof (e.g. the hydrochloride) with a compound of the general formula:

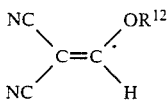  VI wherein $R^{12}$ represents a straight- or branched-chain alkyl radical containing from 1 to 4 carbon atoms, preferably ethyl.

The reaction of a compound of general formula V with a compound of general formula VI may be effected in the presence of an inert organic solvent, for example an alkanol containing from 1 to 4 carbon atoms (e.g. ethanol), acetic acid or ethoxyethanol and at a temperature of from ambient temperature to the reflux temperature of the reaction mixture and optionally in the presence of an alkali metal (e.g. sodium or potassium), acetate, carbonate or bicarbonate. When an acid addition salt of the compound of general formula V is used, the reaction with the compound of general formula VI is effected in the presence of an alkali metal (e.g. sodium or potassium) acetate, carbonate or bicarbonate.

N-Phenylpyrazole derivatives of general formula III, wherein $R^5$, $R^6$, $R^7$, $R^8$ and $R^9$ are as hereinbefore defined and $R^{10}$ represents a cyano radical, may, according to another feature of the present invention, be prepared by reaction of a compound of general formula V with a compound of general formula VI as hereinbefore described without isolation of an intermediate compound of general formula IV from the reaction mixture. When the reaction of a compound of general formula V with a compound of general formula VI is effected in acetic acid, in the absence or presence of an alkali metal (e.g. sodium or potassium) acetate, the intermediate compound of formula IV may separate from the reaction mixture, depending upon the solubility of the intermediate compound of general formula IV in the reaction medium, and may, if desired, be isolated before being cyclised as hereinbefore described to a compound of general formula III, preferably by heating in an inert organic solvent (e.g. ethoxyethanol) at the reflux temperature of the reaction mixture.

Isolated compounds of general formula IV have been found to exhibit herbicidal activities similar to those of the corresponding N-phenylpyrazole derivatives of general formula III into which they may be cyclised, and it is believed that the herbicidal activity of compounds of general formula IV results from their cyclisation to compounds of general formula III.

According to a further feature of the present invention, the N-phenylpyrazole derivatives of general formula III, wherein $R^5$, $R^6$, $R^7$, $R^8$ and $R^9$ are as hereinbefore defined except for the primary amino and cyano radicals and $R^{10}$ represents a substituted carbamoyl group —$CONHR^{11}$ (wherein $R^{11}$ is as hereinbefore defined), are prepared by the selective alkylation of a compound of the general formula:

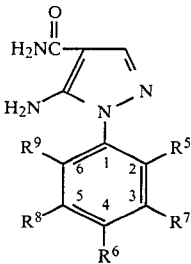  VII (wherein $R^5$, $R^6$, $R^7$, $R^8$ and $R^9$ are as hereinbefore defined except for the primary amino and cyano radicals) with methyl iodide or ethyl iodide, in the presence of an inorganic base.

Compounds of general formula VII (wherein $R^5$, $R^6$, $R^7$, $R^8$ and $R^9$ are as hereinbefore defined, except for the primary amino and cyano radicals) may be prepared from the corresponding compounds of general formula III wherein represents a cyano radical by hydrolysis, for example by treatment with concentrated sulphuric acid.

According to a further feature of the present invention, N-phenylpyrazole derivatives of general formula III, wherein $R^5$, $R^6$, $R^7$, $R^8$ and $R^9$ are as hereinbefore defined and $R^{10}$ represents a substituted carbamoyl group —$CONHR^{11}$ (wherein $R^{11}$ is as hereinbefore defined), are prepared by reaction of a compound of the general formula:

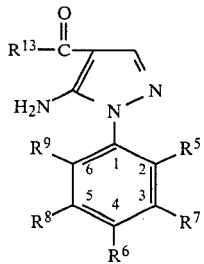  VIII (wherein $R^5$, $R^6$, $R^7$, $R^8$ and $R^9$ are as hereinbefore defined, and $R^{13}$ represents a chlorine atom or a straight- or branched-chain alkoxy radical containing from 1 to 4 carbon atoms) with an amine of the general formula:

$$H_2NR^{11} \qquad \qquad IX$$

wherein $R^{11}$ is as hereinbefore defined.

When $R^{13}$ represents a chlorine atom, reaction of a compound of general formula VIII with an amine of general formula IX is effected at a temperature between ambient temperature and the reflux temperature of the reaction mixture, in the presence of a solvent, which may be an inert organic solvent (e.g. acetone or toluene), or an excess of the amine of general formula IX if the boiling point of the latter is sufficiently high, and optionally in the presence of an acid-binding agent, e.g. sodium bicarbonate, potassium bicarbonate, triethylamine or an excess of the amine of general formula IX.

When $R^{13}$ represents an alkoxy radical, reaction of a compound of general formula VIII with an amine of general formula IX is effected in an inert organic solvent (e.g. ethanol) at a temperature between the reflux temperature of the reaction mixture and 200° C., if necessary at elevated pressure.

Compounds of general formula VIII wherein $R^{13}$ represents a chlorine atom may be prepared by the treatment of a compound of the general formula:

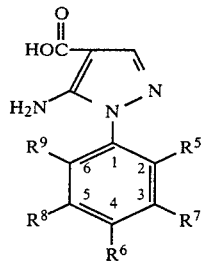

X (wherein the various symbols are as hereinbefore defined) with thionyl chloride, optionally in an inert organic solvent, e.g. toluene or chloroform.

Compounds of general formula VIII wherein $R^{13}$ represents an alkoxy radical may be prepared by the cyclisation of a compound of the general formula:

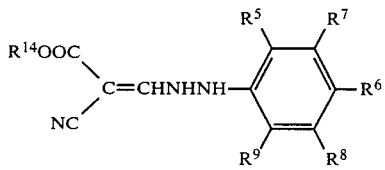

XI wherein $R^5$, $R^6$, $R^7$, $R^8$ and $R^9$ are as hereinbefore defined and $R^{14}$ represents a straight- or branched-chain alkyl group containing from 1 to 4 carbon atoms. Cyclisation may be effected by heating the compound of general formula XI in an inert organic solvent (e.g. ethoxyethanol) at the reflux temperature of the reaction mixture.

Compounds of general formula VIII wherein $R^{13}$ represents an alkoxy radical may also be prepared by the esterification of a compound of general formula X by methods known per se, for example by reaction with the appropriate alcohol in the presence of an inorganic acid. Compounds of general formula X may be prepared by the hydrolysis under alkaline conditions, for example with potassium hydroxide, of the ester group $R^{13}$—CO— of a compound of general formula VIII, wherein $R^{13}$ represents an alkoxy radical and the other symbols are as hereinbefore defined.

Compounds of general formula X may also be prepared from compounds of general formula III wherein $R^{10}$ represents a cyano radical by methods known per se for the hydrolysis of a cyano radical to a carboxy radical, for example by treatment with concentrated hydrochloric acid. Compounds of general formula XI may be prepared by the reaction of a compound of general formula V (wherein the various symbols are as hereinbefore defined) with a compound of the general formula:

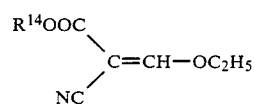

XII wherein $R^{14}$ is as hereinbefore defined. Reaction may be effected at ambient temperature in acetic acid in the presence of sodium carbonate.

Compounds of general formulae V, VI and XII may be prepared by methods known per se.

Acid addition salts of compounds of general formula III wherein at least one of the symbols $R^5$, $R^6$, $R^7$, $R^8$ and $R^9$ represents a primary amino radical may be prepared from the corresponding compounds of general formula III by methods known per se, for example by reacting stoichiometric quantities of the compound of general formula III and the appropriate acid, for example an inorganic, e.g. hydrochloric acid, sulphuric acid, phosphoric acid or nitric acid, or an organic acid, e.g. acetic acid, in a suitable solvent. The acid addition salts may, if necessary, be purified by recrystallization from one, two or more suitable solvents.

As well as being useful in themselves as herbicidally active compounds, acid addition salts of aminophenyl compounds of general formula III may also be used in the purification of the corresponding compounds of general formula III, for example by exploitation of the solubility differences between the salts and the parent compounds in water and in organic solvents, by techniques which are well known to those skilled in the art.

By the term 'methods known per se', as used in the present specification is meant methods heretofore used or described in the chemical literature.

The N-phenylpyrazole derivatives of general formula III wherein $R^5$, $R^6$, $R^7$, $R^8$, $R^9$ and $R^{10}$ are as hereinbefore defined and, when at least one of $R^5$, $R^6$, $R^7$, $R^8$ and $R^9$ represents a primary amino group, acid addition salts thereof, with the exception of 5-amino-4-cyano-1-(2,4-dichlorophenyl)pyrazole and 5-amino-4-cyano-1-(4-chloro-2-methylphenyl)pyrazole, are new compounds which form a further feature of the present invention.

The following Examples and Reference Examples illustrate the preparation of compounds of general formula III.

EXAMPLE 10

Pentafluorophenylhydrazine (10.3 g; described by Stacey et al., J. Chem. Soc. 1960, 1768) was added in portions to a refluxing solution of ethoxymethylenemalononitrile [6.35 g; described by Huber, J. Am. Chem. Soc. 65, 2224 (1943)] in ethanol (23 ml). The solution was heated at reflux for one hour, cooled and diluted with water (23 ml) to precipitate a red solid which was crystallised firstly from aqueous methanol (50 ml, 1:1) and then toluene (25 ml). 5-Amino-4-cyano-1-pentafluorophenylpyrazole (9.8 g), m.p. 152°–153° C., was obtained in the form of brown crystals.

By proceeding in a similar manner but replacing the pentafluorophenylhydrazine by the hereinafter identified appropriately substituted phenylhydrazine, there were prepared:

5-Amino-4-cyano-1-(2,4,6-trifluorophenyl)pyrazole, m.p. 156°–157° C. (after crystallisation from a mixture of ethanol and n-hexane), from 2,4,6-trifluorophenylhydrazine;

5-Amino-4-cyano-1-(2,3,4,6-tetrafluorophenyl)pyrazole, m.p. 176°–177° C. (after crystallisation from toluene), from 2,3,4,6-tetrafluorophenylhydrazine;

5-Amino-4-cyano-1-(2,4-dichlorophenyl)pyrazole, m.p. 136°–137° C. [described by Southwick & Dhawan, J. Heter. Chem., 12, 1200 (1975)];

5-Amino-4-cyano-1-(2,3,4-trichlorophenyl)pyrazole, m.p. 159° C. (after crystallisation from a mixture of toluene and light petroleum, b.p. 100°–120° C.), from 2,3,4-trichlorophenylhydrazine.

5-Amino-4-cyano-1-(2,4,5-trichlorophenyl)pyrazole, m.p. 181°–183° C. (after crystallisation from ethanol), from 2,4,5-trichlorophenylhydrazine [described by Chattaway et al., J. Chem. Soc., 1931, 1925];

5-Amino-4-cyano-1-(2,4,6-trichlorophenyl)pyrazole, m.p. 213°–214° C. (after crystallisation from a mixture of acetone and toluene), from 2,4,6-trichlorophenylhydrazine [described by Chatterway and Irving, J. Chem. Soc., 1931, 1740];

5-Amino-4-cyano-1-(2,4,6-tribromophenyl)pyrazole, m.p. 194°–196° C. (after crystallisation from ethanol), from 2,4,6-tribromophenylhydrazine [described by Neufeld, Ann. 248, 96 (1888)];

5-Amino-4-cyano-1-(2,4-dichloro-5-isopropoxyphenyl)pyrazole, m.p. 198°–199° C. (after crystallisation from toluene), from 2,4-dichloro-5-isopropoxyphenylhydrazine [described in West German patent specification No. 1,795,773 (1976)].

EXAMPLE 11

2,3,4-Trichlorophenylhydrazine (21.15 g) was added in portions to a refluxing solution of ethoxymethylenemalononitrile (12.2 g) in ethanol (100 ml). The solution obtained was then heated at reflux for one hour, cooled and evaporated to dryness. The residue thus obtained was triturated with diethyl ether (100 ml) to give 5-amino-4-cyano-1-(2,3,4-trichlorophenyl)pyrazole (12.6 g), m.p. 158°–160° C., in the form of light brown crystals.

EXAMPLE 12

2,3,4,5-Tetrachlorophenylhydrazine (12.3 g) was heated with ethoxymethylenemalononitrile (6.4 g) in dimethylformamide (25 ml) at reflux for 10 minutes in the presence of sodium carbonate (0.1 g). The hot solution was treated with charcoal and filtered and evaporated to dryness. The residue was triturated with diethyl ether and the ether solution was decanted and diluted with hexane to precipitate dark yellow crystals which were recrystallised from toluene to give 5-amino-4-cyano-1-(2,3,4,5-tetrachlorophenyl)pyrazole (5.3 g), m.p. 168°–169° C., in the form of off-white crystals.

By proceeding in a similar manner but replacing the 2,3,4,5-tetrachlorophenylhydrazine by pentachlorophenylhydrazine [described by Suschitzky et al., J. Chem. Soc., (c) 1971, 167] there was prepared 5-amino-4-cyano-1-pentachlorophenylpyrazole, m.p. 230°–232° C. (after crystallisation from ethanol).

EXAMPLE 13

2,3,4-Trichlorophenylhydrazine (21.15 g) and ethoxymethylenemalononitrile (12.8 g) in ethoxyethanol (100 ml) were heated at reflux for one hour. The solution was then cooled and diluted with water. The sticky solid precipitate thus obtained was crystallized from toluene (48 ml) to give 5-amino-4-cyano-1-(2,3,4-trichlorophenyl)pyrazole (15 g), m.p. 154°–156° C., in the form of off-white crystals.

EXAMPLE 14

2,3,4-Trichlorophenylhydrazine (106 g) was added at laboratory temperature to a stirred solution of anhydrous sodium acetate (20.5 g) in glacial acetic acid (250 ml). Ethoxymethylenemalononitrile (61 g) was then added with stirring to the suspension thus obtained. Partial solution occurrred within 5 minutes, after which a fine precipitate was formed. The mixture was stirred for one hour and then filtered. The solid obtained was washed successively with water, aqueous sodium bicarbonate solution and water and dried to give 2,3,4-trichlorophenylhydrazinomethylenemalononitrile (118 g), m.p. 149°–155° C., in the form of a yellow powder.

The 2,3,4-trichlorophenylhydrazinomethylenemalononitile thus obtained was then heated at reflux for one hour in ethoxyethanol (300 ml). The hot solution was treated with decolourising charcoal, filtered and diluted with water (100 ml). The pale yellow crystals which formed were separated, dried and recrystallised from toluene (400 ml) to give 5-amino-4-cyano-1-(2,3,4-trichlorophenyl)pyrazole (100 g), m.p. 159°–160° C., in the form of colourless crystals.

By proceeding in a similar manner, but replacing the 2,3,4-trichlorophenylhydrazine by the hereinafter indicated appropriately substituted phenylhydrazines, there were prepared:

5-Amino-4-cyano-1-(2-nitro-4-trifluoromethylphenyl)pyrazole m.p. 234°–236° C., in the form of yellow crystals, from 2-nitro-4-trifluoromethylphenylhydrazine [described in West German patent specification No. 2,446,218 (1976)], via 2-nitro-4-trifluoromethylph-enylhydrazinomethylenemalononitrile (isolated as a khaki-coloured powder, m.p. 156°–158° C.);

5-Amino-1-(2-bromo-3,4-dichlorophenyl)-4-cyanopyrazole, m.p. 163°–165° C., in the form of a colourless powder, after crystallisation from toluene, from 2-bromo-3,4-dichlorohenylhydrazine, via 2-bromo-3,4-dichlorophenylhydrazinomethylenemalononitrile (isolated in the form of a cream - coloured powder, m.p. 153°–155° C.);

5-Amino-4-cyano-1-(3,4-dichloro-2-methylphenyl)pyrazole, m.p. 152°–154° C. in the form of a colourless powder, after crystallisation from a mixture of toluene and n-hexane, from 3,4-dichloro-2-methylphenylhydrazine, via 3,4-dichloro-2-methylphenylhydrazinomethylenemalononitrile (isolated in the form of a fawn - coloured powder, m.p. 120°–125° C.);

5-Amino-1-(3-bromo-2,4-dichlorophenyl)-4-cyanopyrazole, m.p. 154°–156° C., in the form of colourless crystals, after crystallisation from toluene, from 3-bromo-2,4-dichlorophenylhydrazine, via 3-bromo-2,4-dichlorophenylhydrazinomethylenemalononitrile (isolated in the form of a cream - coloured powder, m.p. 154°–155° C.);

5-Amino-4-cyano-1-(2,4-dichloro-3-methylphenyl)-pyrazole, m.p. 159°–161° C., in the form of colourless crystals, after crystallisation from toluene, from 2,4-dichloro-3-methylphenylhydrazine, via 2,4-dichloro-3-methylphenylhydrazinomethylenemalononitrile (isolated in the form of a buff - coloured powder, m.p. 132°–134° C.);

5-Amino-4-cyano-1-(3-cyano-2,4-dichlorophenyl)-pyrazole, m.p. 230°–232° C., in the form of colourless crystals, after crystallisation from toluene, from 3-cyano-2,4-dichlorophenylhydrazine, via 3-cyano-2,4-dichlorophenylhydrazinomethylenemalononitrile (isolated as a buff - coloured powder, m.p. 158°–161° C.);

5-Amino-1-(4-bromo-2,3-dichlorophenyl)-4-cyanopyrazole, m.p. 154°155° C., in the form of pale yellow crystals, after crystallisation from toluene, from 4-bromo-2,3-dichloropenylhydrazine, via 4-bromo-2,3-dichlorophenylhydrazinomethylenemalononitrile (isolated as a pale yellow powder, m.p. 148°–151° C.);

5-Amino-1-(4-bromo-2-chloro-3-methylphenyl)-4-cyanopyrazole, m.p. 174°–176° C., in the form of off-white crystals, after crystallisation from toluene, from 4-bromo-2-chloro-3-methylphenylhydrazine, via 4-bromo-2-chloro-3-methylphenylhydrazinomethylenemalononitrile (isolated in the form of a pale brown powder, m.p. 142°–146° C.);

5-Amino-1-(2-chloro-3-cyano-4-methylphenyl)-4-cyanopyrazole, m.p. 206°–209° C., in the form of buff - coloured crystals, after crystallisation from ethanol, from 2-chloro-3-cyano-4-methylphenylhydrazine, via 2-chloro-3-cyano-4-methylphenylhydrazinomethylenemalononitrile (isolated in the form of a buff - coloured powder, m.p. 158°–161° C.);

5-Amino-1-(3-chloro-2,4-dimethylphenyl)-4-cyanopyrazole, m.p. 172°–173° C., in the form of pale brown crystals, from 3-chloro-2,4-dimethylphenylhydrazine, via 3-chloro-2,4-dimethylphenylhydrazinomethylenemalononitrile (isolated as an orange - coloured powder, m.p. 134°–136° C.);

5-Amino-1-(2-bromo-4-chloro-3-methylphenyl)-4-cyanopyrazole, m.p. 167°–169° C., in the form of colourless crystals, after crystallisation from toluene, from 2-bromo-4dichloro-3-methylphenylhydrazine, via 2-bromo-4-chloro-3-methylphenylhydrazinomethylenemalononitrile (isolated in the form of a pale brown powder, m.p. 146°–147° C.);

5-Amino-4-cyano-1-(3-chloro-2,4-difluorophenyl)-pyrazole, m.p. 177° C., in the form of yellow crystals, after crystallisation from toluene, from 3-chloro-2,4-difluorophenylhydrazine, via 3-chloro-2,4-difluorophenylhydrazinomethylenemalononitrile (isolated in the form of a cream coloured powder, m.p. 175° C.).

By proceeding in a similar fashion to that hereinbefore described in the present Example but replacing the 2,3,4-trichlorophenylhydrazine by the hereinafter identified appropriately substituted phenylhydrazine, the following N-phenylpyrazoles according to general formula III were prepared without isolation and cyclisation of an intermediate substituted phenylhydrazinomethylenemalononitrile:

5-Amino-4-cyano-1-(2,4-dichloro-3-methoxyphenyl)-pyrazole, m.p. 185°–187° C., in the form of off-white crystals, after crystallisation from diethyl ether, from 2,4-dichloro-3-methoxyphenylhydrazine;

5-Amino-4-cyano-1-(2,3-dichloro-4-methylphenyl)-pyrazole, m.p. 162°–163° C., in the form of colourless crystals, after crystallisation from a mixture of cyclohexane and ethyl acetate, from 2,3-dichloro-4-methylphenylhydrazine;

5-Amino-1-(2-chloro-3,4-dimethylphenyl)-4-cyanopyrazole, m.p. 179°–181° C., in the form of off-white crystals, after crystallisation from toluene, from 2-chloro-3,4-dimethylphenylhydrazine;

5-Amino-1-(3-chloro-2,4-dibromophenyl)-4-cyanopyrazole, m.p. 171°–172° C., in the form of off-white crystals, after crystallisation from toluene, from 3-chloro-2,4-dibromophenylhydrazine;

5-Amino-1-(4-chloro-2,3-dimethylphenyl)-4-cyanopyrazole, m.p. 167°–170° C., in the form of a salmon - pink coloured solid, from 4-chloro-2,3-dimethylphenylhydrazine;

5-Amino-1-(4-chloro-3-cyano-2-methylphenyl)-4-cyano-pyrazole, m.p. 221°–224° C., in the form of a buff - coloured powder, from 4-chloro-3-cyano-2-methylphenylhydrazine, and 5-Amino-4-cyano-1-(4-trifluoromethylphenyl)pyrazole, m.p. 155°–156.5° C., in the form of a fawn coloured crystalline solid, after recrystallisation from toluene, from 4-trifluoromethylphenylhydrazine.

EXAMPLE 15

Monomethylamine gas was passed for 15 minutes into a stirred solution of 5-amino-1-(2,3,4-trichlorophenyl)-pyrazol-4-yl carbonyl chloride (2.66 g) in tolune (100 ml) at 0° C. The reaction mixture was then allowed to return to laboratory temperature and evaporated to dryness. The brown solid residue thus obtained was triturated with toluene (20 ml), diethyl ether (20 ml) and water (50 ml) to give 5-amino-4-N-methylcarbonamido-1-(2,3,4-trichlorophenyl)pyrazole (1.1 g), m.p. 224°–226° C., in the form of a fawn coloured powder.

By proceeding in a similar fashion but replacing the monomethylamine by an excess of monoethylamine, there was prepared 5-amino-4-N-ethylcarbonamido-1-(2,3,4-trichlorophenyl)pyrazole, m.p. 241°–242° C., in the form of colourless crystals, after crystallisation from toluene.

REFERENCE EXAMPLE 1

Phenylhydrazines used in the preparation of N-phenylpyrazole derivatives according to general formula III described in Examples 10 to 15 were prepared as follows:

(a) 2,3,4,6-Tetrafluoroaniline (27.5 g) was diazotised with sodium nitrite (12.5 g) in a mixture of concentrated hydrochloric acid (580 ml) and glacial acetic acid (110 ml). The filtered diazonium salt solution was reduced by the addition of a solution of stannous chloride dihydrate (108 g) in concentrated sulphuric acid (108 ml) at 0°–10° C. The resulting hydrazine hydrochloride solution was evaporated to dryness and the residue was dissolved in water and basified by the addition of aqueous ammonia solution (S.G. 0.880). The precipitated solid was filtered off and the filter pad was well washed with diethyl ether. The ethereal washings were combined with ether extracts of the filtrate, dried over sodium sulphate, filtered and evaporated to dryness. Trituration of the residue with hexane gave 2,3,4,6-tetrafluorophenylhydrazine (18.3 g), m.p. 74°–76° C., in the form of off-white crystals.

By proceeding in a similar manner but replacing the 2,3,4,6-tetrafluoroaniline by 2,4,6-trifluoroaniline there was prepared 2,4,6-trifluorophenylhydrazine, m.p. 57°–58° C. (after crystallisation from aqueous methanol). By proceeding in a similar manner but replacing the 2,3,4,6-tetrafluoroaniline by 2,3,4-trichloroaniline there was prepared, after filtration of the insoluble hydrazine hydrochloride, 2,3,4-trichlorophenylhydrazine, m.p. 142°–143° C. By proceeding in a similar manner but replacing the 2,3,4,6-trifluoroaniline by 4-trifluoromethylaniline, there was prepared, after filtration of the insoluble hydrazine hydrochloride, 4-trifluoromethylphenylhydrazine, m.p. 63°–65° C., in the form of light brown crystals.

(b) 2,3,4,5-Tetrachloroaniline (23.1 g) was heated at 55°–60° C. in glacial acetic acid (125 ml) to which a solution of sodium nitrite (7.9 g) in concentrated sulphuric acid (60 ml) was added over 15 minutes. After the addition, heating at 60° C. was maintained for 15 minutes and the solution was cooled to 0°–5° C. A solution of stannous chloride dihydrate (87.5 g) in concentrated hydrochloric acid (75 ml) was added at less than 10° C. and the voluminous precipitate was filtered off and washed with saturated aqueous sodium chloride solution. The solid was treated with a mixture of ice and aqueous ammonia (S.G. 0.880) to give a solid white mass which was removed by filtration and dried at 80° C. The white powder was extracted with chloroform in a Soxhlet apparatus to give, after evaporation, 2,3,4,5-tetrachlorophenylhydrazine (21 g), m.p. 172°–176° C.

(c) 2,3,4-Trichloroaniline (100 g) was dissolved with stirring in glacial acetic acid (875 ml) at 55°–60° C. A solution of sodium nitrite (39.5 g) in concentrated sulphuric acid (300 ml) was then added over 15 minutes at 55°–60° C. to the solution thus obtained. The viscous mixture obtained was cooled to 5°–10° C. and a solution of stannous chloride dihydrate (437 g) in concentrated hydrochloric acid (375 ml) was added at 5°–10° C. over 20 minutes. A fine, off-white solid precipitated. To aid filtration, the mixture was warmed to 60° C., allowed to cool to laboratory temperature and then filtered. The precipitate was washed on the filter with saturated aqueous sodium chloride solution (100 ml). The damp powder thus obtained was added to a stirred mixture of aqueous ammonia (1.3 liters; S.G. 0.880) and ice. The fine slurry which formed was filtered and the precipitate obtained was dried at 80° C., and boiled twice with chloroform (2×1.5 liters). The chloroform extracts were combined and evaporated to dryness to give 2,3,4-trichlorophenylhydrazine (86 g), m.p. 142°–143° C., in the form of a colourless powder.

By proceeding in a similar manner, but replacing the 2,3,4-trichloroaniline by the appropriate substituted aniline, there were prepared:

2-Bromo-3,4-dichlorophenylhydrazine, m.p. 143°–146° C., in the form of off-white crystals, from 2-bromo-3,4-dichloroaniline;
3,4-Dichloro-2-methylphenylhydrazine, m.p. 105°–106° C., in the form of a buff-coloured powder, from 3,4-dichloro-2-methylaniline (described by Sylvester and Wynne, J. Chem. Soc., 1936, 694);
3-Bromo-2,4-dichlorophenylhydrazine, m.p. 128°–130° C., in the form of a pink crystalline solid, from 3-bromo- 0 2,4-dichloroaniline [described by Hurtley, J. Chem. Soc., 79, 1302 (1901)];
2,4-Dichloro-3-methylphenylhydrazine, m.p. 58°–60° C., in the form of yellow crystals, from 2,4-dichloro-3-methylaniline [described by Cohen and Dakin, J. Chem. Soc., 81, 1332 (1902)];
2,4-Dichloro-3-methoxyphenylhydrazine, m.p. 88°–90° C., in the form of brown crystals, from 2,4-dichloro-3-methoxyaniline;
3-Cyano-2,4-dichlorophenylhydrazine, m.p. 199°–200° C., in the form of a yellow powder, from 3-cyano-2,4-dichloroaniline [described by N. V. Philips Gloelampenfabricken, Chem. Abs., 75, P 5527K (1971)];
4-Bromo-2,3-dichlorophenylhydrazine, m.p. 135°–137° C., in the form of a cream-coloured powder, from 4-bromo-2,3-dichloroaniline [described by Hurtley, J. Chem. Soc., 79, 1302 (1901)];
2,3-Dichloro-4-methylphenylhydrazine, m.p. 111°–114° C., in the form of colourless crystals, from 2,3-dichloro-4-methylaniline (described by Sylvester and Wynne, J. Chem. Soc., 1936, 691);
4-Bromo-2-chloro-3-methylphenylhydrazine, m.p. 100°–103° C., in the form of colourless solid, from 4-bromo-2-chloro-3-methylaniline;
2-Chloro-3,4-dimethylphenylhydrazine, m.p. 71°–73° C., in the form of a buff-coloured powder, from 2-chloro-3,4-dimethylaniline (described by Hinkel et al., J. Chem. Soc., 1934, 286);
2-Chloro-3-cyano-4-methylphenylhydrazine, m.p. 168°–170° C., in the form of a colourless powder, from 2-chloro-3-cyano-4-methylaniline;
3-Chloro-2,4-dibromophenylhydrazine, m.p. 148°–150° C., in the form of brown crystals, after crystallisation from ethanol, from 3-chloro-2,4-dibromoaniline [described by Hurtley, J. Chem. Soc., 79, 1304 (1901)];
3-Chloro-2,4-dimethylphenylhydrazine, m.p. 104° C., in the form of a yellow powder, from 3-chloro-2,4-dimethylaniline [described by Staskin, Tetrahedron Letters, 5069 (1972)];
2-Bromo-4-chloro-3-methylphenylhydrazine, m.p. 72°–73° C., in the form of an off-white powder, from 2-bromo-4-chloro-3-methylaniline; 4-Chloro-2,3-dimethylphenylhydrazine, m.p. 69°–71° C., in the form of a pale yellow powder, from 4-chloro-2,3-dimethylaniline (described by Hinkel et al., J. Chem. Soc., 123, 2968 (1923);
4-Chloro-3-cyano-2-methylphenylhydrazine, m.p. 184°–187° C., in the form of colourless crystals, from 4-chloro-3-cyano-2-methylaniline, and
2,3,4,5-Tetrachlorophenylhydrazine, m.p. 172°–176° C., in the form of a colourless powder, from 2,3,4,5-tetrachloroaniline.

REFERENCE EXAMPLE 2

Substituted anilines, not hitherto described in the chemical literature, used in the preparation of substituted phenylhydrazines as hereinbefore described in Reference Example 1 were prepared as follows:

(a) A solution of 2-bromo-3,4-dichloronitrobenzene (23.5 g) in toluene was treated at 25°–35° C. for 1.25 hours with hydrogen in the presence of charcoal containing 5% platinum. The solution was then filtered and the filtrate was evaporated to dryness. The brown solid thus obtained was dissolved in diethyl ether and the solution was treated with decolourising charcoal and filtered. Evaporation to dryness of the filtrate gave 2-bromo-3,4-dichloroaniline (18.0 g), m.p. 78°–80° C. in the form of a brown powder.

By proceeding in a similar manner but replacing the 2-bromo-3,4-dichloronitrobenzene by the appropriately substituted nitrobenzene hereinafter indicated, there were prepared:

2,4-Dichloro-3-methoxyaniline, in the form of a dark oil, from 2,4-dichloro-3-methoxynitrobenzene [described by Mallory and Varimbi, J. Org. Chem., 28,1656 (1963)];

4-Bromo-2-chloro-3-methylaniline, m.p. 51°–52° C., in the form of light brown crystals, from 4-bromo-2-chloro-3-methylnitrobenzene, and 2-Bromo-4-chloro-3-methylaniline, m.p. 64°–65° C., in the form of an off-white solid, from 2-bromo-4-chloro-3-methylnitrobenzene.

(b) A solution of 2-chloro-6-methyl-3-nitrobenzonitrile (6.3 g) in ethanol (23 ml) was added to a solution of stannous chloride dihydrate (21.7 g) in concentrated hydrochloric acid (19 ml). The mixture was then heated at reflux for 15 minutes, cooled and diluted with water (200 ml). The fine white powder which precipitated was separated, dried and crystallized from ethanol (10 ml) to give 2-chloro-3-cyano-4-methylaniline (1.7 g), m.p. 117°–119° C., in the form of colourless crystals.

By proceeding in a similar manner, but replacing the 2-chloro-6-methyl-3-nitrobenzonitrile by 6-chloro-2-methyl-3-nitrobenzonitrile, 4-chloro-3-cyano-2-methylaniline, m.p. 133°–134° C., was obtained in the form of fluffy colourless crystals, after crystallisation from toluene.

REFERENCE EXAMPLE 3

Substituted nitrobenzenes, not hitherto described in the chemical literature, used in the preparation of substituted anilines as hereinbefore described in Reference Example 2, were prepared as follows: (a) 2,3-Dichloro-6-nitroaniline [29 g; prepared by a modification (reaction at 125° C.) of the procedure described by Beilstein and Kurbatow, Ann., 192, 235 (1878)] was dissolved with stirring at 55°–60° C. in glacial acetic acid (350 ml). A solution of sodium nitrite (11 g) in concentrated sulphuric acid (80 ml) was then added to the solution thus obtained with stirring over 15 minutes at a temperature of 55°–60° C. maintained by intermittent cooling with water. The red solution obtained was cooled to 15° C. and poured, with stirring, into a solution of cuprous bromide (20 g) in concentrated hydrobromic acid (200 ml) and ice (500 g). The mixture was allowed to attain laboratory temperature, heated for one hour at 60° C. and then steam-distilled. The distillate obtained was extracted with diethyl ether (6×500 ml). The combined ethereal extracts were washed successively with aqueous sodium hydroxide solution (2N; 3×750 ml and water (2×500 ml), dried over anhydrous sodium sulphate and filtered. The filtrate was evaporated to dryness to give a yellow powder, which was then crystallised from hexane (125 ml) to give 2-bromo-3,4-dichloronitrobenzene (26.7 g), m.p. 73° C., in the form of yellow crystals.

By proceeding in a similar manner but replacing the 2,3-dichloro-6-nitroaniline by the appropriately substituted anilines hereafter indicated, there were prepared:

4-Bromo-2-chloro-3-methylnitrobenzene, m.p. 59°–60° C., in the form of yellow crystals, from 3-chloro-2-methyl-4-nitrbaniline, and 2-Bromo-4-chloro-3-methylnitrobenzene, m.p. 43°–44° C., in the form of yellow crystals, from 3-chloro-2-methyl-6-nitroaniline.

(b) 6-Chloro-2-methylbenzonitrile (29.7 g) was added in small portions at −15° to −10° C., with stirring, to fuming nitric acid (150 ml; S.G. 1.52). The solution obtained was maintained at this temperature for 10 minutes, then allowed to stand at laboratory temperature for 24 hours and then poured on to ice (500 g). The yellow precipitate obtained was filtered off, washed with water and dried to give a mixture of nitrobenzonitriles (36.2 g), m.p. 76°–80° C. The mixture of nitrobenzonitriles obtained (27.8 g) was chromatographed on a silica column (1 kg) eluted with a mixture of hexane and gradually increasing amounts (from 10% to 25% by volume) of ethyl acetate.

Evaporation of the eluate containing the faster-moving component gave 6-chloro-2-methyl-3-nitrobenzonitrile (20 g), m.p. 89°–91° C., in the form of fluffy colourless crystals. Evaporation of the eluate containing the slower-moving component gave 2-chloro-6-methyl-3-nitrobenzonitrile (6 g), m.p. 106°–107° C., in the form of a cream-coloured powder. (It is reported in British patent specification No. 1,141,249 (1969), that nitration of 6-chloro-2-methylbenzonitrile gives exclusively a product described as 6-chloro-2-methyl-3-nitrobenzonitrile, m.p. 75°–80° C. However, the procedure described above leads unequivocally to the two products which were obtained).

REFERENCE EXAMPLE 4

The chloro-methyl-nitroanilines used in the preparation of bromo-chloro-methylnitrobenzenes as hereinbefore described in Reference Example 3 were prepared as follows:

3-Chloro-o-toluidine (90 g) in a mixture of glacial acetic acid (90 ml) and acetic anhydride (90 ml) was heated on a steam bath for 10 minutes. The solution obtained was then poured into water. A colourless powder precipitated, which was filtered off and dried to give 3-chloro-2-methylacetanilide (104 g), m.p. 156°–159° C., which was then dissolved with stirring in concentrated sulphuric acid (230 ml), while maintaining the temperature at not more than 30° C. The stirred solution was maintained at 5°–10° C. whilst concentrated nitric acid (38 ml; S.G. 1.42) was added during 30 minutes. The solution obtained was then stirred at 0° C. for one hour and then poured on to ice. The solid precipitate which was obtained was separated by filtration, washed with water and dried, to give a mixture of nitroacetanilides (145 g), m.p. 135°–147° C., in the form of a yellow powder. This mixture of nitroacetanilides (94 g) was then heated at reflux for 6 hours in a mixture of glacial acetic acid (560 ml) and concentrated hydrochloric acid (370 ml). The mixture was then cooled, poured into water (1200 ml) and basified by the addition of aqueous 50% sodium hydroxide solution. The yellow precipitate which was obtained was separated by filtration, washed with water and dried, to give a mixture of nitroanilines (72 g), m.p. 150°–164° C. This mixture was then steam-distilled in the presence of concentrated hydrochloric acid (200 ml). The solid which separated from the distillate was filtered off to give 3-chloro-2-methyl-4-nitroaniline (19.1 g), m.p. 152°–154° C., in the form of a yellow solid. Further steam distillation gave a distillate containing a mixture of products (8.6 g), m.p. 134°–138° C. The insoluble material, which had not been distilled, was separated from the acid solution to give 3-chloro-2-methyl-6-nitroaniline (18 g), m.p. 164°–165° C., in the form of a brown powder.

REFERENCE EXAMPLE 5

5-Amino-1-(2,3,4-trichlorophenyl)pyrazol-4-yl carbonyl chloride used in the preparation of N-phenylpyrazole derivatives according to general formula III described in Example 15 was prepared as follows:

5-Amino-1-(2,3,4-trichlorophenyl)pyrazol-4-yl carboxylic acid (54 g) and thionyl chloride (75 ml) were heated together under reflux for one hour. The reaction mixture was then evaporated to dryness and residual thionyl chloride was removed by evaporation in the presence of toluene (3×200 ml) to give 5-amino-1-(2,3,4-trichlorophenyl)pyrazol-4-yl carbonyl chloride, in the form of a dark coloured oil which was used in the preparation described in Example 11 without further purification.

5-Amino-1-(2,3,4-trichlorophenyl)pyrazol-4-yl carboxylic acid used in the above preparation was prepared as follows:

2,3,4-Trichlorophenylhydrazine (53 g) and ethyl 2-cyano-3-ethoxyprop-2-enoate [45.6 g: described by De Bollemont, Compte Rendu, 128, 1339 (1899)] were added to a stirred solution of sodium acetate (10 g) in acetic acid (150 ml) at laboratory temperature. After stirring for 30 minutes, the reaction mixture was diluted with diethyl ether (500 ml) and the solid material was removed by filtration. The separated solid was suspended in diethyl ether (500 ml) and filtered to give ethyl 2-cyano-3-(2,3,4-trichlorophenylhydrazo)prop-2-enoate (70 g), m.p. 177°–178° C., in the form of a colourless crystalline solid.

Ethyl 2-cyano-3-(2,3,4-trichlorophenylhydrazo)-prop-2-enoate (70 g) was heated under reflux in ethoxyethanol (375 ml) for 1.5 hours. The hot solution was then filtered and the filtrate was diluted with water (1.5 liters). The solid which precipitated was removed by filtration to give ethyl 2-amino-1-(2,3,4-trichlorophenyl)pyrazol-4-ylcarboxylate (65 g), m.p. 158°–159° C., in the form of a colourless crystalline solid.

Ethyl 2-amino-1-(2,3,4-trichlorophenyl)pyrazol-4-ylcarboxylate prepared as described above (73 g) was heated under reflux in a solution of potassium hydroxide (120 g) in water (1 liter) for 4 hours with vigorous stirring. The orange coloured solution thus obtained was then filtered. The filtrate was washed with diethyl ether (2×500 ml) and acidified to pH 1 by the addition of concentrated hydrochloric acid. The solid which precipitated was separated by filtration, washed with water and dried, to give 5-amino-1-(2,3,4-trichlorophenyl)-pyrazol-4-yl carboxylic acid (52 g), m.p. 186° C. (with decomposition), in the form of a cream coloured powder.

2,3,4,6-Tetrafluoroaniline, 2,3,4-trichloroaniline and 2,3,4,5-tetrachloroaniline, used in the preparation of substituted phenylhydrazines as hereinbefore described in Reference Example 1, and 6-chloro-2-methylbenzonitrile, used in the preparation of chloromethylnitrobenzonitriles as hereinbefore described in Reference Example 3, are known compounds which are readily available.

EXAMPLE 16

2,6-Dichloro-4-ethylphenylhydrazine (2.54 g) was added in one portion to a stirred solution of ethoxymethylenemalononitrile [1.55 g; described by Huber. J. Amer. Chem. Soc., 65, 2224 (1943)] and anhydrous sodium acetate (0.5 g) in glacial acetic acid (12 ml) at laboratory temperature. A fine precipitate formed after 5 minutes and stirring was continued for 2 hours. The reaction mixture was allowed to stand at laboratory temperature overnight then filtered. The solid product was washed successively with a small quantity of glacial acetic acid, saturated aqueous sodium bicarbonate solution and water, to give 2,6-dichloro-4-ethylphenylhydrazinomethylenemalononitrile (1.41 g), m.p. 137°–138° C., in the form of a fawn coloured solid.

The 2,6-dichloro-4-ethylphenylhydrazinomethylenemalononitrile thus obtained was heated at reflux for 1 hour in ethoxyethanol (15 ml). The hot solution was filtered and the filtrate diluted with water (15 ml) and the solid precipitate filtered off to give 5-amino-4-cyano-1-(2,6-dichloro-4-ethylphenyl)pyrazole (1.15 g), m.p. 189°–190° C., in the form of fawn-coloured crystals.

By proceeding in a similar manner, but replacing the 2,6-dichloro-4-ethylphenylhydrazine by the hereinafter identified appropriately substituted phenylhydrazine, there was prepared:

5-Amino-1-(2-chloro-4-ethylphenyl)-4-cyanopyrazole, m.p. 174°–175° C., after crystallisation from toluene, in the form of light orange crystals, from 2-chloro-4-ethylphenylhydrazine, via 2-chloro-4-ethylphenylhydrazinomethylenemalononitrile.

EXAMPLE 17

4-Methyl-2,3,5,6-tetrafluorophenylhydrazine [29.8; described by Burdon et al, J. Chem. Soc., 5152 (1965)] was added in one portion to a solution of ethoxymethylenemalononitrile (19 g) and anhydrous sodium acetate (5.3 g) in glacial acetic acid (65 ml) stirred at laboratory temperature. After stirring at laboratory temperature for 1 minute, a fine precipitate formed and stirring at laboratory temperature was continued for 4 hours. The reaction mixture was then allowed to stand overnight at laboratory temperature, diluted with water (50 ml) and filtered. The solid precipitate was washed successively with glacial acetic acid, water, saturated aqueous sodium bicarbonate solution and water, to give 4-methyl-2,3,5,6-tetrafluorophenylhydrazinomethylenemalononitrile (37 g) m.p. 140°–143° C., in the form of a yellow solid.

The 4-methyl-2,3,5,6-tetrafluorophenylhydrazinomethylenemalononitrile thus obtained was heated at reflux for 45 minutes in ethoxyethanol (50 ml). The hot solution was treated with charcoal and filtered. The filtrate was cooled, diluted with water (20 ml) and the solid precipitate was filtered off and washed with water to give 5-amino-4-cyano-1-(4-methyl-2,3,5,6-tetrafluorophenyl)pyrazole (26 g), m.p. 169°–170° C., in the form of a yellow solid.

By proceeding in a similar manner, but replacing the 4-methyl-2,3,5,6-tetrafluorophenylhydrazine by the hereinafter identified appropriately substituted phenylhydrazine, there was prepared:

5-Amino-1-(2-chloro-4-methylphenyl)-4-cyanopyrazole, m.p. 143°–144° C., in the form of fawn-coloured crystals, from 2-chloro-4-methylphenylhydrazine, m.p. 70°–72° C. [described by Bulow and Engler, Ber. 52, 639 (1919)], via 2-chloro-4-methylphenylhydrazinomethylenemalononitrile (isolated in the form of a fawn-coloured solid, m.p. 133°–134° C.).

REFERENCE EXAMPLE 6

Phenylhydrazines used as starting materials in Example 16 were prepared as follows:

2-Chloro-4-ethylaniline [14.5 g; described by K. Altau, J. Chem. Eng. Data, 8, 122 (1963)] was dissolved, with stirring, in glacial acetic acid (113 ml). A solution of sodium nitrite (7.0 g) in concentrated sulphuric acid (55 ml) was then added at 55°–60° C. The solution thus obtained was cooled to 0°–5° C. and a solution of stannous chloride (70 g) in concentrated hydrochloric acid (80 ml) was added with vigorous stirring. A cream-coloured solid precipitated. The mixture was filtered and the solid obtained was added to a mixture of aqueous ammonium hydroxide solution and ice. The mixture thus obtained was extracted with diethyl ether (4×300 ml) and the combined ethereal extracts were dried over sodium sulphate, filtered and evaporated to dryness, to give 2-chloro-4-ethylphenylhydrazine (9.6 g), m.p. 55°–57° C., in the form of a cream-coloured solid.

By proceeding in a similar manner, but replacing the 2-chloro-4-ethylaniline by the hereinafter indicated appropriately substituted aniline, there was prepared:

2,6-Dichloro-4-ethylphenylhydrazine, m.p. 48°–50° C., in the form of a cream-coloured solid, from 2,6-dichloro-4-ethylaniline;

REFERENCE EXAMPLE 7

2,6-Dichloro-4-ethylaniline used as a starting material in Reference Example 1 was prepared as follows:

A solution of 4-amino-3,5-dichloroacetophenone [15.8 g; described by Lutz et al, J. Org. Chem., 12, 617 (1947)] in glacial acetic acid (100 ml) and sulphuric acid (d:1.84; 8.2 g) was treated at 22°–27° C. for 22.5 hours with hydrogen in the presence of charcoal containing 5% palladium and filtered. The filtrate was evaporated to dryness and the yellow solid thus obtained was suspended in ice-water (150 ml). Aqueous sodium hydroxide solution (20% w/v) was added to pH10 and the mixture was then extracted with diethyl ether (3×150 ml). The ethereal extracts were combined, washed with water, dried over anhydrous sodium sulphate and evaporated to dryness. The yellow solid (11.75 g) thus obtained was chromatographed on a silica column (Merck, 250–400 mesh; pressure 25 lb in$^{-2}$) eluated with hexane-toluene (5:1). Evaporation of the eluate containing the faster-moving component gave 2,6-dichloro-4-ethylaniline (4.59 g), m.p. 47°–48° C., in the form of colourless crystals.

EXAMPLE 18

By proceeding in a similar manner to that hereinbefore described in Example 16 but replacing the 2,6-dichloro-4-ethyl-phenylhydrazine by the hereinafter identified appropriately substituted phenyl-hydrazine, there were prepared:

5-Amino-4-cyano-1-(4-methyl-2,3,6-trichlorophenyl)-pyrazole, m.p. 187.5°–189.5° C., in the form of off-white crystals, from 4-methyl-2,3,6-trichlorophenylhydrazine, via 4-methyl-2,3,6-trichlorophenylhydrazinomethylenemalononitrile (isolated in the form of a cream-coloured solid, m.p. 145°–147° C.).

5-Amino-4-cyano-1-(2,3-dichloro-4-ethylphenyl)-pyrazole, m.p. 152°–154° C., in the form of a colourless solid, from 2,3-dichloro-4-ethylphenylhydrazine, via 2,3-dichloro-4-ethylphenylhydrazinomethylenemalononitrile (isolated in the form of a cream-coloured solid, m.p. 138°–140° C.).

5-Amino-1-(2-chloro-4-n-propylphenyl)cyanopyrazole, m.p. 117°–118° C., in the form of a fawn-coloured solid, from 2-chloro-4-n-propylphenylhydrazine via 2-chloro-4-n-propylphenylhydrazinomethylenemalononitrile (isolated in the form of a colourless solid, m.p. 136°–137° C.).

5-Amino-4-cyano-1-(2,6-dibromo-4-trifluoromethylphenyl)-pyrazole, m.p. 187°–188° C., in the form of a colourless solid, from 2,6-dibromo-4-trifluoromethylphenylhydrazine, via 2,6-dibromo-4-trifluoromethylphenylhydrazinomethylenemalononitrile (isolated in the form of a cream-coloured solid, m.p. 174°–175° C.).

5-Amino-1-(2-chloro-4-isopropylphenyl) cyanopyrazole, m.p. 180°–182° C., after crystallization from toluene, in the form of fawn-coloured crystals, from 2-chloro-4-isopropylphenylhydrazine, via 2-chloro-4-isopropylphenylhydrazinomethylenemalononitrile.

5-Amino-1-(4-n-butyl-2,3,5,6-tetrafluorophenyl)-4-cyano-pyrazole, m.p. 123°–124° C., after crystallization from toluene, in the form of colourless crystals, from 4-n-butyl-2,3,5,6-tetrafluorophenylhydrazine, via 4-n-butyl-2,3,5,6-tetrafluorophenylhydrazinomethylenemalononitrile.

5-Amino-4-cyano-1-(4-ethyl-2,3,5,6-tetrafluorophenyl)-pyrazole, m.p. 145.5°–146.5° C., after crystallization from toluene, in the form of colourless crystals, from 4-ethyl-2,3,5,6-tetrafluorophenylhydrazine, via 4-ethyl-2,3,5,6-tetrafluorophenylhydrazinomethylenemalononitrile.

REFERENCE EXAMPLE 8

4-n-Butyl-2,3,5,6-tetrafluorophenylhydrazine, used as starting material in Example 18, was prepared as follows:

n-Butylpentafluorobenzene [19.0 g; described by J. M. Birchall and R. N. Haszeldine J. Chem. Soc p 3719 (1961)] was added to a solution of hydrazine hydrate (50 ml; 99–100% w/w) in ethanol (100 ml) and the mixture heated at reflux for 72 hours. The reaction mixture was cooled, evaporated to dryness to give a solid which was filtered off and washed with ethanol and hexane to give 4-n-butyl-2,3,5,6-tetrafluorophenylhydrazine (20.5 g), m.p. 80°–81° C., in the form of colourless crystals.

REFERENCE EXAMPLE 9

The following phenylhydrazines used as starting materials in Example 18 were prepared as follows:

By proceeding in a similar manner to that hereinbefore described in Reference Example 6 but replacing the 2-chloro-4-ethylaniline by the hereinafter indicated appropriately substituted aniline, there were prepared:
4-Methyl-2,3,6-trichlorophenylhydrazine, m.p. 131°–133° C., in the form of a white solid, from 4-methyl-2,3,6-trichloroaniline [described by F. Bell, J. Chem. Soc. p 2376, (1955)]. 2,6-Dibromo-4-trifluoromethylphenylhydrazine, m.p. 65°–67° C., in the form of a fawn-coloured solid, from 2,6-dibromo-4-trifluoromethylaniline (prepared as described hereinafter in Reference Example 14).

REFERENCE EXAMPLE 10

The following phenylhydrazine used as a starting material in Example 18 was prepared as follows:

By proceeding in a similar manner to that hereinbefore described in Reference Example 8 but replacing the n-butylpentafluorobenzene by the hereinafter indicated appropriately substituted benzene, there was prepared:
4-Ethyl-2,3,5,6-tetrafluorophenylhydrazine, m.p. 82°–83° C., in the form of colourless crystals, from ethylpentafluorobenzene [described by R. J. Harper et al J. Org. Chem. 29, 2385 (1964)].

REFERENCE EXAMPLE 11

The following phenylhydrazines used as starting materials in Example 18 were prepared as follows:

A solution of 2-chloro-4-isopropylacetanilide (9.3 g) in a mixture of glacial acetic acid (66 ml) and hydrochloric acid (44 ml; density 1.19) was heated at reflux for 4 hours. After cooling, the reaction mixture was stirring and a solution of sodium nitrite (3.72 g) in concentrated sulphuric acid (27 ml) added at 15°–20° C. The solution thus obtained was cooled to 0°–5° C. and a solution of stannous chloride (40 g) in concentrated hydrochloric acid (35 ml) was added with vigorous stirring. A cream-coloured precipitate formed. The mixture was filtered and the solid obtained basified with aqueous sodium hydroxide (2N, 350 ml). This was extracted with dichloromethane (3×200 ml) and the combined extracts washed with water (2×500 ml), dried over anhydrous magnesium sulphate and evaporated to dryness to give 2-chloro-4-isopropylphenylhydrazine (4.5 g), m.p. 64°–66° C., in the form of a colourless solid. The filtrate from the stannous-complex filtration was reduced under diminished pressure and the residue basified with aqueous sodium hydroxide (50% w/v), ice being added to maintain the temperature at 20°–25° C. The mixture was similarly extracted with dichloromethane to furnish a further quantity of 2-chloro-4-isopropylphenylhydrazine (3.03 g), m.p. 65°–67° C., in the form of a yellow solid.

By proceeding in a similar manner but replacing 2-chloro-4-isopropylacetanilide by the hereinafter appropriately substituted acetanilide, there were prepared:
2,3-Dichloro-4-ethylphenylhydrazine, m.p. 80°–82° C., in the form of a yellow solid, from 2,3-dichloro-4-ethylacetanilide. 2-Chloro-4-n-propylphenylhydrazine, in the form of an brown oil, from 2-chloro-4-n-propylacetanilide.

REFERENCE EXAMPLE 12

Sodium hypochlorite (60 ml; bleach grade 14–15% w/v available chlorine) was added to a solution of 3-chloro-4-ethylacetanilide [5-g; described by J. P. Lambooy J. Med. Chem. 16 765 (1973)] in a mixture of glacial acetic acid (10 ml), ethanol (10 ml) and water (10 ml). An exothermic reaction occurred resulting in the precipitation of an orange oil. The aqueous layer was decanted and the oil dissolved in diethyl ether and the ether was washed with water, saturated aqueous sodium bicarbonate solution, water and then dried over anhydrous magnesium sulphate and was evaporated to dryness to give an oil which partially crystallized on standing. The orange semi-solid (4.27 g) thus obtained was chromatographed on a silica column (Merck, 250–400 mesh, pressure 25 lb in$^{-2}$) eluted with dichloromethane-ethyl acetate (19:1), fractions being taken every 25 ml. Evaporation of the eluate (fractions 12+13) containing the faster moving component gave 2,5-dichloro-4-ethylacetanilide (0.8 g), m.p. 113°–114° C. in the form of a colourless solid. Evaporation of the eluate (fractions 16–20) containing the slower moving component gave 2,3-dichloro-4-ethylacetanilide (1.39 g), m.p. 94°–96° C., in the form of a colourless solid. Evaporation of the remaining eluate (fractions 24–37 gave recovered 3-chloro-4-ethylacetanilide (1.0 g), m.p. 100°–101° C., in the form of a colourless solid.

By proceeding in a similar manner, but replacing the 3-chloro-4-ethylacetanilide by the hereinafter appropriately substituted acetanilide and chromatographing the crude product using the eluent hereinafter defined there was prepared:

2-Chloro-4-n-propylacetanilide, m.p. 78°–79° C., after crystallization from ethanol-water, in the form of colourless crystals, after chromatography of the crude product using dichloromethane as eluent, from p-n-propylacetanilide [described by Willgeralt, Ann. 327 307 (1903)].

REFERENCE EXAMPLE 13

Acetic anhydride (21 ml) was added to a solution of 4-isopropylaniline (27 g) in glacial acetic acid (62 ml) and the reaction mixture heated at reflux for 1½ hours. The solution was then stirred and cooled to 10° C. and concentrated hydrochloric acid (67 ml) added. The reaction mixture was then stirred vigorously while a solution of sodium chlorate (6.7 g) in water (18 ml was added dropwise at 15°–20° C. and the stirring continued at laboratory temperature for 6 hours. After standing at room temperature overnight the reaction mixture was poured onto ice-water (1.51) to precipitate a brown solid which was filtered off and washed with water. The solid was chromatographed on a silica column (Merck, 250–400 mesh; pressure 25 lb in$^{-2}$) using dichloromethane-ethyl acetate (15:1) as eluent. Evaporation of the eluate containing the faster moving component gave 2-chloro-4-isopropylacetanilide (9.76 g), m.p. 115°–116° C., in the form of a fawn-coloured solid.

REFERENCE EXAMPLE 14

Bromine (96 g) was added dropwise to a stirred mixture of 4-aminobenzotrifluoride (48.3 g) and reduced iron (3 g) in ethyl acetate (300 ml) at a temperature of 30°–50° C. The solution was then heated at reflux for 1 hour, after which evolution of hydrogen bromide ceased. The reaction mixture was evaporated to dryness and the residue dissolved in diethyl ether (1.51) and basified with aqueous sodium hydroxide (2N) to pH 14. The organic layer was removed and the aqueous layer extracted with diethyl ether (500 ml). The ether extracts were combined, washed with water (2×500 ml) and dried over anhydrous sodium sulphate, then evaporated to give a brown semi-solid (90.0 g). The semi-solid was treated with hexane (50 ml) and filtered; the filtrate was cooled to −30° C. to precipitate a solid which was removed by filtration to give 2,6-dibromo-4-trifluoromethylaniline (65.4 g), m.p. 37°–39° C., in the form of fawn-coloured crystals.

EXAMPLE 19

By proceeding in a similar manner to that hereinbefore described in Example 17 but replacing the 4-methyl-2,3,5,6-tetrafluorophenylhydrazine by the hereinafter identified appropriately substituted phenylhydrazine, there were prepared:

5-Amino-4-cyano-1-(3,5-difluoro-2,4,6-trichlorophenyl)pyrazole, m.p. 210°–212° C., after crystallisation from toluene, in the form of a colourless solid, from 3,5-difluoro-2,4,6-trichlorophenylhydrazine [described by. N. Ishikawa, Nippon Kagaku Zasshi 86, 1202 (1965)] via 3,5-difluoro-2,4,6-trichlorophenylhydrazinomethylenemalononitrile.

5-Amino-4-cyano-1-(2,4-dichloro-6-methylphenyl) pyrazole, m.p. 199°–202° C., after crystallisation from toluene in the form of a colourless solid, from 2,4-dichloro-6-methylphenylhydrazine (described in British Pat. No. 904,852) via 2,4-dichloro-6-methyl-phenylhydrazinomethylenemalononitrile (isolated in the form of an off-white solid, m.p. 151°–153° C.).

5-Amino-1-(4-bromo-2,3,5,6-tetrafluorophenyl)-4-cyanopyrazole, m.p. 208°–210° C., after crystallisation from toluene, in the form of a colourless solid, from 4-bromo-2,3,5,6-tetrafluorophenylhydrazine [described by J. Burdon. Tet. Lett. 22, 1183 (1966)] via 4-bromo-2,3,5,6-tetrafluorophenylhydrazinomethylenemalononitrile.

5-Amino-1-(4-chloro-2,3,5,6-tetrafluorophenyl)-4-cyanopyrazole, m.p. 164°–166° C., after crystallisation from toluene, in the form of a colourless solid, from 4-chloro-2,3,5,6-tetrafluorophenylhydrazine [described by N. Ishikawa. Nippon Kagaku Zasshi 89 321 (1968)] via 4-chloro-2,3,5,6-tetrafluorophenylhydrazinomethylenemalononitrile.

5-Amino-1-(2-bromo-4-trifluoromethylphenyl)-4-cyanopyrazole, m.p. 194°–196° C., after crystallisation from toluene in the form of colourless crystals, from 2-bromo-4-trifluoromethylphenylhydrazine, via 2-bromo-4-trifluoromethylphenylhydrazinomethylenemalononitrile.

5-Amino-1-(4-sec-butyl-2,3,5,6-tetrafluorophenyl)-4-cyanopyrazole, m.p. 125.5°–127° C., after crystallisation from toluene, in the form of colourless crystals, from 4-sec-butyl-2,3,5,6-tetrafluorophenylhydrazine via 4-sec-butyl-2,3,5,6-tetrafluorophenylhydrazinomethylenemalononitrile.

5-Amino-4-cyano-1-(2,3,4,6-tetrachlorophenyl)-pyrazole, m.p. 193°–194° C., in the form of a colourless crystalline solid, from 2,3,4,6-tetrachlorophenylhydrazine [described by Chattaway et al J. Chem. Soc. p 1925 (1931)] via 2,3,4,6-tetrachlorophenylhydrazinomethylenemalononitrile (isolated in the form of a fawn coloured solid, m.p. 174°–176° C.).

REFERENCE EXAMPLE 15

The following phenylhydrazine used as starting material in Example 19 was prepared as follows:

By proceeding in a similar manner to that hereinbefore described in Reference Example 6 but replacing the 2-chloro-4-ethylaniline by the hereinafter indicated appropriately substituted aniline, there was prepared:

2-Bromo-4-trifluoromethylphenylhydrazine, in the form of a red oil, from 2-bromo-4-trifluoromethylaniline (described in U.S. Pat. No. 3,995,042, Pharm Doc 94181X).

REFERENCE EXAMPLE 16

The following phenylhydrazine used as starting material in Example 19 was prepared as follows:

By proceeding in a similar manner to that hereinbefore described in Reference Example 8 but replacing the n-butylpentafluorobenzene by the hereinafter appropriately substituted pentafluorobenzene, and adding sufficient dioxan to the reaction mixture to obtain a homogeneous solution, there was obtained:

4-sec-Butyl-2,3,5,6-tetrafluorophenylhydrazine, m.p. 23°–29° C., in the form of a yellow waxy solid, from sec-butylpentafluorobenzene.

REFERENCE EXAMPLE 17

4-sec-Butylpentafluorobenzene, used as a starting material in Reference Example 16, was prepared as follows:

A solution of sec-butyl lithium (350 ml; 12% in cyclohexane) was added over a period of 1 hour to a stirred mixture of hexafluorobenzene (80 g) in cyclohexane (750 ml) at a temperature of 0° C. On warming the reaction above 0° C. a violently exothermic reaction took place which was brought under control by external cooling (Cardice-acetone). The reaction mixture was subsequently brought to room temperature (no further reaction occurred) and was quenched with water (600 ml). The organic layer was separated, washed with dilute hydrochloric acid (2N; 2×200 ml) and water (2×200 ml) and dried over anhydrous magnesium sulphate and distilled through a 15 cm vigreux column. The fraction distilling at 160°–170° C. was collected to give sec-butylpentafluorobenzene (50.3 g), b.p. 162°–164° C. (760 mm), in the form of a colourless liquid. Hexafluorobenzene is a known compound and is readily available.

We claim:

1. A method of controlling the growth of weeds at a locus which comprises applying to the locus a herbicidally effective amount of an N-phenylpyrazole derivative in a herbicidal composition which comprises, as active ingredient, an effective amount of an N-phenylpyrazole derivative of the formula:

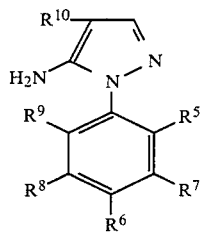

(wherein each of $R^5$ and $R^6$ represents an alkyl or alkoxy radical of 1 through 4 carbon atoms, a trifluoromethyl, trifluoromethoxy, nitro, cyano or primary amino radical or a fluorine, chlorine or bomine atom, each of $R^7$, $R^8$ and $R^9$ represents a hydrogen atom, an alkyl or alkoxy radical of 1 through 4 carbon atoms, a trifluoromethyl, trifluoromethoxy, nitro, cyano or primary amino radical or a fluorine, chlorine or bromine atom, or $R^5$, $R^7$, $R^8$ and $R^9$ each represents a hydrogen atom and $R^6$ represents a trifluoromethoxy or trifluoromethyl radical and $R^{10}$ represents a cyano radical or substituted carbamoyl radical —CONHR$^{11}$, wherein $R^{11}$ represents a methyl or ethyl radical), or when at least one of symbols $R^5$, $R^6$, $R^7$, $R^8$ and $R^9$ represents a primary amino radical or an agriculturally acceptable acid addition salt thereof, in association with one or more capatible herbicidally-acceptable diluents or carriers.

2. A method according to claim 1 in which the active ingredient is an N-phenylpyrazole derivative of the formula depicted in claim 1 wherein each of $R^5$ and $R^6$ represents an alkyl radical of 1 through 4 carbon atoms, a trifluoromethyl or nitro radical, or a fluorine, chlorine or bromine atom.

3. A method according to claim 1 in which the active ingredient is an N-phenylpyrazole derivative of the formula depicted in claim 1 wherein $R^7$ represents a hydrogen atom, an alkyl or alkoxy radical of 1 through 4 carbon atoms, a cyano radical or a fluorine, chlorine or bromine atom.

4. A method according to claim 1 in which the active ingredient is an N-phenylpyrazole derivative of the formula depicted in claim 1 wherein each of $R^8$ and $R^9$ represents a hydrogen atom or a fluorine, chlorine or bromine atom.

5. A method according to claim 1, 2, 3 or 4 in which the active ingredient is an N-phenylpyrazole derivative of the formula depicted in claim 1 wherein $R^{10}$ represents a cyano radical.

6. A method according to claim 1 in which the active ingredient is an N-phenylpyrazole derivative of the formula depicted in claim 1 wherein $R^8$ and $R^9$ represent hydrogen atoms.

7. A method according to claim 1 in which the active ingredient is an N-phenylpyrazole derivative of the formula depicted in claim 1 wherein each of $R^5$ and $R^6$ represents an alkyl radical or 1 through 4 carbon atoms, a trifluoromethyl or nitro radical, or a fluorine, chlorine or bromine atom, $R^7$ represents a hydrogen atom, an alkyl or alkoxy radical of 1 through 4 carbon atoms, a cyano radical, or a fluorine, chlorine or bromine atom, $R^8$ and $R^9$ represent hydrogen atoms, and $R^{10}$ is as defined in claim 1.

8. A method according to claim 1 in which the active ingredient is an N-phenylpyrazole derivative of the formula depicted in claim 1 wherein each of $R^5$ and $R^6$ represents a methyl, trifluoromethyl or nitro radical or a fluorine, chlorine or bromine atom, $R^7$ represents a methyl, methoxy or cyano radical or a fluorine, chlorine or bromine atom, $R^8$ and $R^9$ represent hydrogen atoms and $R^{10}$ is as defined in claim 1.

9. A method according to claim 7 or 8 wherein $R^{10}$ represents a cyano radical.

10. A method according to claim 1, 2, 3, 4, 6 or 7 wherein the alkyl radicals within the definition of $R^5$, $R^6$, $R^7$, $R^8$ and $R^9$ are methyl.

11. A method according to claim 1, 2, 3, 4, 6 or 7 wherein the alkoxy radicals within the definition of $R^5$, $R^6$, $R^7$, $R^8$ and $R^9$ are methoxy.

12. A method according to claim 1, 2, 3, 4, 6, 7 or 8 in which the active ingredient is an N-phenylpyrazole derivative of the formula depicted in claim 1 wherein $R^{10}$ represents a carbamoyl group —CONHCH$_3$.

13. A method according to claim 7 or 8 in which the active ingredient is an N-phenylpyrazole derivative of the formula depicted in claim 1 wherein at least one of the symbols $R^5$, $R^6$ and $R^7$ represents a chlorine atom.

14. A method according to claim 1 in which the active ingredient is 5-amino-4-cyano-1-(2,3,4-trichlorophenyl)pyrazole.

15. A method according to claim 1 in which the active ingredient is 5-amino-4-cyano-1-(2,4-dichlorophenyl)pyrazole.

16. A method according to claim 1 in which the active ingredient is at least one N-phenylpyrazole derivative selected from 5-amino-1-(2-bromo-3,4-dichlorophenyl)-4-cyanopyrazole, 5-amino-4-cyano-1-(3,4-dichloro-2-methylphenyl)pyrazole, 5-amino-1-(3-bromo-2,4-dichlorophenyl)-4-cyanopyrazole, 5-amino-4-cyano-1-(2,4-dichloro-3-methylphenyl)pyrazole, 5-amino-4-cyano-1-(2,4-dichloro-3-methoxyphenyl)pyrazole, 5-amino-4-cyano-1-(3-cyano-2,4-dichlorophenyl)pyrazole, 5-amino-1-(bromo-2,3-dichlorophenyl)-4-cyanopyrazole, 5-amino-4-cyano-1-(2,3-dichloro-4-methylphenyl)pyrazole, 5-amino-4-cyano-1-(4-bromo-2-chloro-3-methylphenyl)pyrazole, 5-amino-4-cyano-1-(2-chloro-3,4-dimethylphenyl)pyrazole, 5-amino-4-cyano-1-(2-chloro-3-cyano-4-methylphenyl)pyrazole, 5-amino-1-(3-chloro-2,4-dibromophenyl)-4-cyanopyrazole, 5-amino-1-(3-chloro-2,4-dimethylphenyl)-4-cyanopyrazole, 5-amino-1-(2-bromo-4-chloro-3-methylphenyl)-4-cyanopyrazole, 5-amino-1-(4-chloro-2,3-dimethylphenyl)-4-cyanopyrazole and 5-amino-1-(4-chloro-3-cyano-2-methylphenyl)-4-cyanopyrazole.

17. A method according to claim 1 in which the active ingredient is at least one N-phenylpyrazole derivative selected from 5-amino-4-cyano-1-(2,6-dichloro-4-ethylphenyl)pyrazole, 5-amino-1-(2-chloro-4-ethylphenyl)-4-cyanopyrazole, 5-amino-4-cyano-1-(4-methyl-2,3,5,6-tetrafluorophenyl)pyrazole, 5-amino-1-(2-chloro-4-methylphenyl)-4-cyanopyrazole, 5-amino-4-cyano-1-(4-methyl-2,3,6-trichlorophenyl)pyrazole, 5-amino-1-(4-n-butyl-2,3,5,6-tetrafluorophenyl)-4-cyanopyrazole, 5-amino-1-(2-chloro-4-isopropylphenyl)-4-cyanopyrazole, 5-amino-4-cyano-1-(2,3-dichloro-4-ethylphenyl)pyrazole, 5-amino-4-cyano-1-(4-ethyl-2,3,5,6-tetrafluorophenyl)pyrazole, 5-amino-1-(2-chloro-4-n-propylphenyl)-4-cyanopyrazole, 5-amino-4-cyano-1-(2,6-dibromo-4-trifluoromethylphenyl)pyrazole, 5-amino-4-cyano-1-(3,5-difluoro-2,4,6-trichlorophenyl)pyrazole, 5-amino-4-cyano-1-(2,4-dichloro-6-methylphenyl)pyrazole, 5-amino-1-(4-bromo-2,3,5,6-tetrafluorophenyl)-4-cyanopyrazole, 5-amino-1-(4-chloro-2,3,5,6-tetrafluorophenyl)-4-cyanopyrazole, 5-amino-1-(2-bromo-4-trifluoromethylphenyl)-4-cyanopyrazole, 5-amino-1-(4-sec-butyl-2,3,5,6-tetrafluorophenyl)-4-cyanopyrazole and 5-amino-4-cyano-1-(2,3,4,6-tetrachlorophenyl)pyrazole.

18. A method according to claim 1 in which the herbicidal composition comprises from 0.05 to 90% by weight of the said N-phenylpyrazole derivative.

19. A method according to claim 8 in which the weeds are broad-leafed weeds, selected from the group consisting of *Aethusa cynapium, Abutilon theophrasti, Amaranthus retroflexus, Amsinckia intermedia, Anagallis arvensis, Anthemis arvensis, Atriplex patula, Bidens pilosa, Brassica nigra, Capsella bursa-pastoris, Chenopodium album, Chrysanthemum segetum, Cirsium arvense, Datura stamonium, Desmodium tortuosum, Emex australis, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata,* Polygonum spp.,(eg. *Polygonum aviculare, Polygonum convolvulus and Polygonum persicaria), Portulaca oleracea, Raphanusraphanistrum, Rotala indica, Rumex obtusifolius, Saponaria vaccaria, Scandix pectenveneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Xanthium strumarium.*

20. A method according to claim 1 in which the weeds are grass weeds, selected from the group consisting of *Alopecurus myosuroides, Apera spica-venti, Agrostis stolonifera, Avena fatua, Avena ludoviciana,* Brachiaria spp., *Bromus sterilis, Bromus tectorum, Cenchrus spp., Cynodon dactylon, Digitaria sanguinalis, Echinochloa crus-galli, Eleusine indica, Setaria viridis* and *Sorghum halepense.*

21. A method according to claim 1, 19 or 20 wherein the N-phenylpyrazole derivative is applied pre- or post-emergence of the weeds.

22. A method according to claim 1 in which the herbicidal composition is applied to an area used, or to be used, for growing crops.

23. A method according to claim 22 in which the herbicidal composition is applied to a crop-growing area at a rate sufficient to control the growth of weeds without causing, substantial permanent damage to the crop.

24. A method according to claim 1 in which the N-phenylpyrazole derivative is applied at a rate between 0.1 kg and 20 kg per hectare.

25. A method according to claim 22 or 23 in which the crop is a cereal, soya beans, field or dwarf beans, peas, lucerne, cotton, peanuts, flax, onions, carrots, cabbage, oilseed rape, sunflower, sugar beet, or permanent or sown grassland.

26. A method according to claim 22 or 23 in which the crop is wheat, barley, oats, maize or rice.

27. A method according to claim 22 in which the N-phenylpyrazole derivative is applied at a rate between 0.25 kg and 8.0 kg per hectare.

28. A method according to claim 24 or 27 in which the N-phenylpyrazole derivative is applied at a rate between 0.5 kg and 2.0 kg per hectare.

29. A method according to claim 27 in which the herbicidal composition is applied for the control of broad-leafed weeds in an area used for growing a cereal crop before or after emergence of both the crop and weeds.

30. A method according to claim 29 in which the herbicidal composition is applied post-emergence of the broad-leafed weeds.

* * * * *